(12) United States Patent
Zhang et al.

(10) Patent No.: US 7,923,557 B2
(45) Date of Patent: Apr. 12, 2011

(54) PROCESS FOR PREPARING TRISUBSTITUTED PYRIMIDINE COMPOUNDS

(75) Inventors: Shijie Zhang, Nashua, NH (US); Elena Kostik, Arlington, MA (US); Lijun Sun, Harvard, MA (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 1269 days.

(21) Appl. No.: 11/271,568

(22) Filed: Nov. 10, 2005

(65) Prior Publication Data

US 2006/0122209 A1    Jun. 8, 2006

Related U.S. Application Data

(60) Provisional application No. 60/626,609, filed on Nov. 10, 2004.

(51) Int. Cl.
| | | |
|---|---|---|
| C07D 239/34 | (2006.01) | |
| C07D 239/38 | (2006.01) | |
| C07D 239/50 | (2006.01) | |
| A61K 31/505 | (2006.01) | |
| A61K 31/506 | (2006.01) | |
| A61P 19/02 | (2006.01) | |

(52) U.S. Cl. ........ 544/317; 544/323; 544/324; 544/309; 544/319

(58) Field of Classification Search .......... 544/309, 544/317, 323, 324
See application file for complete search history.

(56) References Cited

U.S. PATENT DOCUMENTS

| | | | |
|---|---|---|---|
| 6,384,032 B1 | 5/2002 | Ono et al. | |
| 6,660,733 B2 | 12/2003 | Sun et al. | |
| 6,693,097 B2 * | 2/2004 | Ono et al. | 514/227.8 |
| 6,858,606 B2 | 2/2005 | Sun et al. | |
| 6,958,332 B2 | 10/2005 | Sun et al. | |
| 7,045,517 B2 | 5/2006 | Ono et al. | |
| 7,067,514 B2 | 6/2006 | Ono et al. | |
| 7,122,665 B2 | 10/2006 | Sun et al. | |
| 7,338,951 B2 | 3/2008 | Ono et al. | |
| 2005/0250770 A1 | 11/2005 | Ono et al. | |
| 2005/0250787 A1 | 11/2005 | Sun et al. | |
| 2005/0282809 A1 | 12/2005 | Ono et al. | |
| 2006/0025409 A1 | 2/2006 | Ono et al. | |
| 2006/0030560 A1 | 2/2006 | Sun et al. | |
| 2007/0027151 A1 | 2/2007 | Sun et al. | |

FOREIGN PATENT DOCUMENTS

| | | |
|---|---|---|
| WO | WO-00/62778 | 10/2000 |
| WO | WO-00/78757 | 12/2000 |

OTHER PUBLICATIONS

Nishigaki et al. "Synthesis of Iminodipyrimidines", Tetrahedron Letters. 7:539-542 (1969).
International Search Report for International Application No. PCT/US05/40712, Apr. 21, 2006.

* cited by examiner

*Primary Examiner* — Venkataraman Balasubramanian
(74) *Attorney, Agent, or Firm* — Edwards Angell Palmer & Dodge LLP; Jeffrey D. Hsi; Mark D. Russett

(57) ABSTRACT

Disclosed herein is a regioselective synthesis of compounds represented by formula (I):

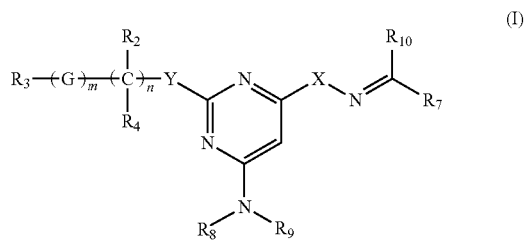

or a salt, solvate, clathrate, or prodrug thereof, wherein X, Y, $R_2$, $R_3$, $R_4$, $R_7$, $R_8$, $R_9$, $R_{10}$, m and n are defined as within.

8 Claims, No Drawings

US 7,923,557 B2

PROCESS FOR PREPARING TRISUBSTITUTED PYRIMIDINE COMPOUNDS

RELATED APPLICATIONS

This application claims the benefit of U.S. Provisional Application No. 60/626,609, filed on Nov. 10, 2004, the entire teachings of which are incorporated herein by reference.

FIELD OF THE INVENTION

The present invention relates to a method for the production of compounds useful for immunosuppression and in the treatment or prevention of immune disorders, inflammatory disorders and allergic disorders. In particular, the invention relates to a method for the production of trisubstituted pyrimidine compounds.

BACKGROUND OF THE INVENTION

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547.

Over-production of IL-12 causes excessive Th1 responses, and may result in inflammatory diseases and immune disorders, such as insulin-dependent diabetes mellitus, multiple sclerosis, rheumatoid arthritis, psoriasis, Crohn's disease, or sepsis. See, for example, Gately et al. (1998) *Annu Rev Immunol.* 16: 495; and Abbas et al. (1996) *Nature* 383: 787. Thus, inhibiting IL-12 production is an approach to treat the just-mentioned diseases. Trembleau et al. (1995) *Immunol. Today* 16: 383; and Adorini et al. (1997) *Chem. Immunol.* 68: 175. For example, production of IL-12 and the resultant excessive Th1 type responses can be suppressed by modulating IL-12 production. A compound that down-regulates IL-12 production can be used for treating or preventing inflammatory diseases. Ma et al. (1998) *Eur Cytokine Netw* 9: 54. In addition, IL-12 has been implicated in promoting various immune diseases (see for example, Segal et al. (1998) J. Exp. Med. 187:4, 537-546 and Williamson et al., J. Immunol. (1997) 159: 15, 1208-1215). Accordingly, a compound that inhibits IL-12 production can be used for treating or preventing immune diseases.

IL-12 also plays a role in bone loss diseases, particularly those involving osteoclasts. Osteoclasts are unique multinucleated cells within bone that are responsible for bone degradation and resorption. These are the only cells in the body known to be capable of this function. Osteoclasts have a high capacity for the synthesis and storage of enzymes, including acid hydrolases and carbonic anhydrase isoenzyme II. Osteoclasts share phenotypic characteristics with circulating monocytes and tissue macrophages (N. Kurihara et al., Endocrinology 126: 2733-41 (1990); G. Hattersley et al, Endocrinology 128: 259-62 (1991)). These cells are derived from mononuclear precursors that are the progeny of stem-cell populations located in the bone marrow, spleen, and liver. Proliferation of these stem-cell populations produces osteoclastic precursors, which migrate via vascular routes to skeletal sites. These cells then differentiate and fuse with each other to form osteoclasts, or alternatively, fuse with existing osteoclasts.

The regulation of osteoclastic formation and activity is only partly understood but it is known that excessive bone resorption by osteoclasts contributes to the pathology of many human diseases associated with excessive bone loss, including periodontal disease, non-malignant bone disorders (such as osteoporosis, Paget's disease of bone, osteogenesis imperfecta, fibrous dysplasia, and primary hyperparathyroidism) estrogen deficiency, inflammatory bone loss, bone malignancy, arthritis, osteopetrosis, and certain cancer-related disorders (such as hypercalcemia of malignancy (HCM), osteolytic bone lesions of multiple myeloma and osteolytic bone metastases of breast cancer and other metastatic cancers).

There is a continuing unmet need for new therapeutics to treat the aforementioned conditions. Trisubstituted pyrimidine compounds disclosed, for example, in U.S. Pat. No. 6,693,097, filed on Nov. 30, 2001, U.S. Pat. No. 6,660,733, filed on Jul. 10, 2002, U.S. patent application Ser. No. 10/305, 039, filed on Nov. 26, 2002, U.S. application Ser. No. 10/656, 671, filed on Sep. 5, 2003, U.S. application Ser. No. 10/655, 672, filed on Sep. 5, 2003 and U.S. Provisional Application No. 60/585,124, filed on Jul. 1, 2004, the entire teachings of the aforementioned patents and patent applications are incorporated herein by reference, have demonstrated efficacy in inhibiting the production of IL-12 and, thus, are useful in treating inflammatory diseases and autoimmune diseases. Disclosed syntheses of trisubstituted pyrimidine compounds produce a mixture of regioisomers wasting a portion of the starting materials in the production of undesirable isomers, and sacrificing some of the desired isomeric product in the separation of the undesirable isomers from the desired product. Therefore, a need exists for improved (e.g., more efficient, less costly, safer, more convenient, higher yielding, higher purity, etc.) methods to produce trisubstituted pyrimidine compounds (and compositions thereof) useful for inhibiting the production of IL-12 and in treating diseases or disorders related to the over production of IL-12.

SUMMARY OF THE INVENTION

The present invention relates to a regioselective synthesis of compounds represented by formula (I):

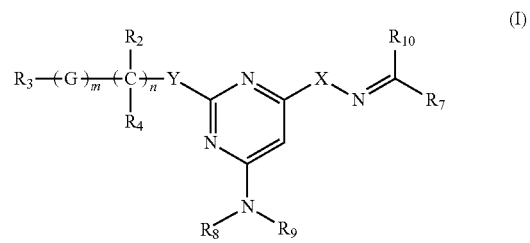

or a salt, solvate, clathrate, or prodrug thereof, wherein:
X is —O—, —S—, —NH—, or —NR$^e$—;
G is —O—, —C(O)NHNH—, —NHNHC(O)—, —C(O)NR$^f$NR$^g$—, —NR$^f$NR$^g$C(O)—, —CH=N—NH—, —NH—N=CH—, —CR$^g$=N—NR$^f$—, —NR$^f$—N=CR$^g$—, —NHNH—, —NR$^f$NR$^g$—, —NHO—, —O—NH—, —O—NR$^c$—, —NR$^c$—O—, —CH=N—O—, —O—N=CH—, —CR$^f$=N—O—, —O—N=CR$^f$—, —O—C(O)—NH—, —O—C(O)—NR$^f$—, —O—C(S)—

—NH—, —NH—C(S)—O—, —O—C(S)—NR$^f$—, —NR$^c$C(S)—O—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R$^c$)—NH—, —NH—C(O)—NH—, —NR$^c$—C(O)—NR$^c$—, —NH—C(S)—NH— and —NR$^c$—C(S)—NR$^c$—, —NH—S(O)$_2$—NH—, —NRC—S(O)$_2$—NR$^c$—, —N(R$^c$)—S(O)$_2$—O—, —P(O)(R$^c$)—, —P(O)(R$^c$)—O—, —P(O)(R$^c$)—NR$^c$—, -Cyclyl-, -Heterocycloalkyl-, -Aryl-, -Heteroaryl-, -Heteroaralkyl-, -Heteroaryl-NH—, -Heteroaryl-S—, -Heteroaralkyl-O—, —C(N—CN)—NH—, —Si(OH)$_2$—, —B(OH)—, —C(NH)—NR$^c$—, —N(R$^c$)—CH$_2$—C(O), —C(O)—ON(R$^c$)—, —C(O)—N(R$^c$)O—, —C(S)—ON(R$^c$)—, —C(S)—N(R$^c$)O—, —C(N(R$^d$))—ON(R$^c$)—, —C(N(R$^d$))—NR$^c$O—, —OS(O)$_2$—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)$_2$O—, —N(R$^c$)N(R$^c$)C(S)O—, —N(R$^c$)N(R$^c$)C(N(R$^d$))O—, —OP(O)$_2$O—, —N(R$^c$)P(O)$_2$O—, —OP(O)$_2$N(R$^c$)—, —N(R$^c$)P(O)$_2$N(R$^c$)—, —P(O)$_2$O—, —P(O)$_2$N(R$^c$)—, —N(R$^c$)P(O)$_2$—, —OP(O)$_2$—, —alkyl-heterocycloalkyl-N(R$^c$)—, —N(R$^c$)CHR$^d$C(O)N(R$^c$)CHR$^d$C(O)—, —N(R$^c$)CHR$^d$C(O)—N(R$^c$)C(O)CHR$^d$, or —C(O)N(R$^c$)CHR$^d$C(O)—; wherein R$^f$, R$^g$ and R$^h$, for each occurrence is H, alkyl, aryl, heteroaryl, aralkyl, cycloalkyl, or heterocycloalkyl;

R$_2$ and R$_4$, for each occurrence, are, independently, R$^c$, alkenyl, alkynyl, halogen, nitro, cyano, isothionitro, SR$^c$, or OR$^c$; or R$_2$ and R$_4$, taken together with the carbon to which they are attached, are a carbonyl;

R$_3$ is R$^c$, alkenyl, alkynyl, —OR$^c$, —OC(O)R$^c$, —SO$_2$R$^c$, —S(O)R$^c$, —S(O)$_2$NR$^c$R$^d$, —SR$^c$, —NR$^c$R$^d$, —NR$^c$COR$^d$, —NR$^c$C(O)R$^d$, —NR$^c$C(O)OR$^d$, —NR$^c$C(O)NR$^c$R$^d$, —NR$^c$SO$_2$R$^d$, —C(O)R$^c$, —C(O)OR$^c$, —C(O)NR$^c$R$^d$, —P(O)OR$^c$OR$^d$, or s(O)$_2$NR$^c$R$^d$;

R$_7$ is an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; and R$_8$ and R$_9$ are each, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R$_8$ and R$_9$ taken together with the nitrogen to which they are attached are an optionally substituted heterocycloalkyl or an optionally substituted heteroaryl;

R$_{10}$ is H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl;

n is 0, 1, 2, 3, 4, 5, or 6;
m is 0 or 1;
Y is O, S, or NR$^c$;
R$^c$ and R$^d$, for each occurrence, are, independently, H, alkyl, aryl, aralkyl, heteroaryl, heteroaralkyl, cycloalkyl, heterocycloalkyl, —C(O)-alkyl, or —S(O)$_2$R$_f$; and
R$^e$ is a lower alkyl.

In one embodiment, the method for regioselectively preparing a compound represented by formula (I) comprises the steps of:

a) reacting HNR$_8$R$_9$ with a 2,4,6-trihalopyrimidine in a solvent, wherein HNR$_8$R$_9$ is present in an excess amount compared to the 2,4,6-trihalopyrimidine, to form a first mixture of isomers represented by formulas (IIIa) and (IIIb):

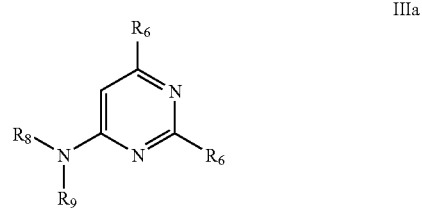

IIIa

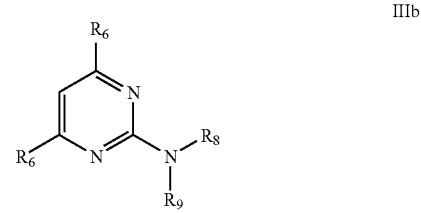

IIIb wherein R$_6$, for each occurrence, is independently F, Cl, Br, or I; and b) adding a strong base to a mixture comprising a polar solvent, the isomers represented by formulas (IIIa) and (IIIb) and a compound represented by formula (II):

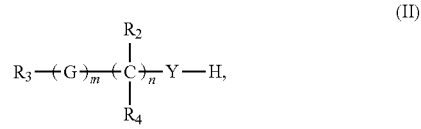

(II)

thereby forming a second mixture of isomers represented by formulas (IVa), (IVb), and (IVc):

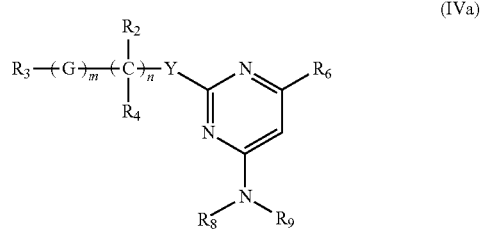

(IVa)

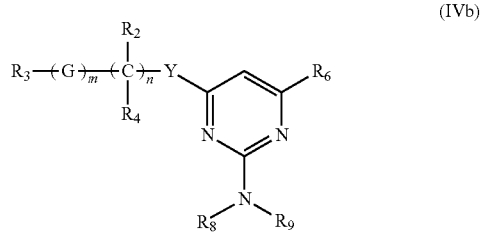

(IVb)

(IVc)

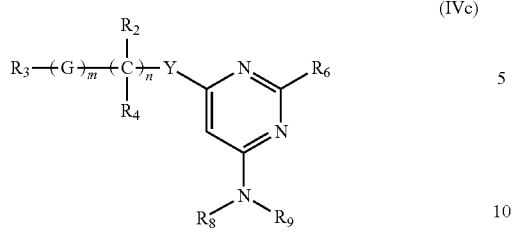

c) adding water to the second mixture of isomers, thereby selectively precipitating the compound represented by formula (IVa);

d) collecting the precipitate comprising a compound represented by formula (IVa);

e) heating a suspension comprising hydrazine, $NH_2$—$NHR^e$, $NH_2$—$NHR^i$, HO—$NHR^i$, or HS—$NHR^i$, wherein $R^i$ is an amine protecting group, and the precipitate comprising a compound represented by formula (IVa), thereby forming a compound represented by formula (VIa):

(VIa)

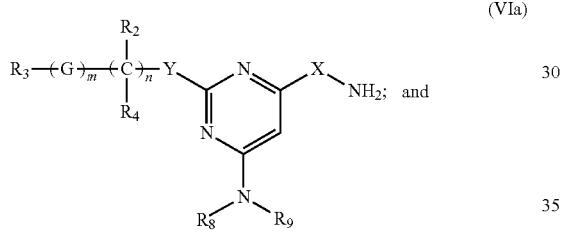

f) heating in the presence of a catalytic amount of an acid the compound represented by formula (VIa) and a compound represented by the formula $R_7$—$C(O)R_{10}$, thereby regioselectively forming a compound represented by formula (I).

In one embodiment, the precipitate collected in step d) is a substantially pure regioisomer represented by formula (IVa).

In another embodiment, the method for regioselectively preparing a compound represented by formula (I) comprises the steps of:

a) reacting $HNR_8R_9$ with a 2,4,6-trihalopyrimidine in a solvent, wherein $HNR_8R_9$ is present in an excess amount compared to the 2,4,6-trihalopyrimidine, to form a first mixture of isomers represented by formulas (IIIa) and (IIIb):

IIIa

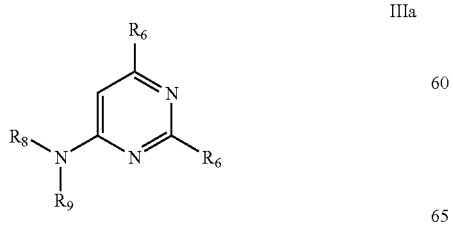

IIIb

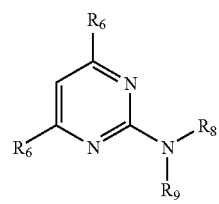

wherein $R_6$, for each occurrence, is independently F, Cl, Br, or I; and b) adding a strong base to a mixture comprising the isomers represented by formulas (IIIa) and (IIIb) and a compound represented by formula (II):

(II)

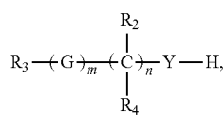

thereby forming a second mixture of isomers represented by formulas (IVa), (IVb), and (IVc):

(IVa)

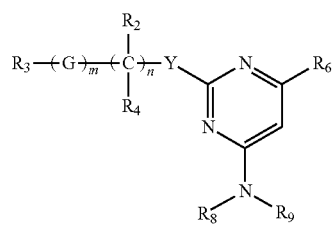

(IVb)

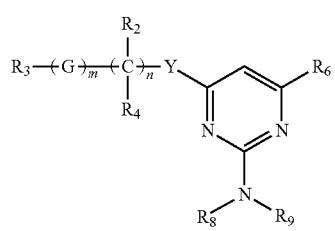

(IVc)

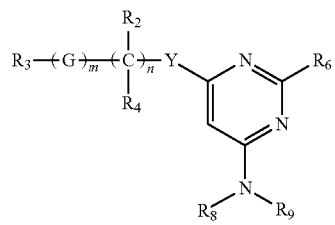

c) heating a suspension comprising hydrazine, $NH_2NHR^e$, $NH_2$—$NHR^i$, HO—$NHR^i$, or HS—$NHR^i$, and the isomers represented by formulas (IVa), (IVb), and (IVc) in a polar solvent, thereby forming a mixture comprising isomers represented by formulas (VIa), (VIb) and (VIc):

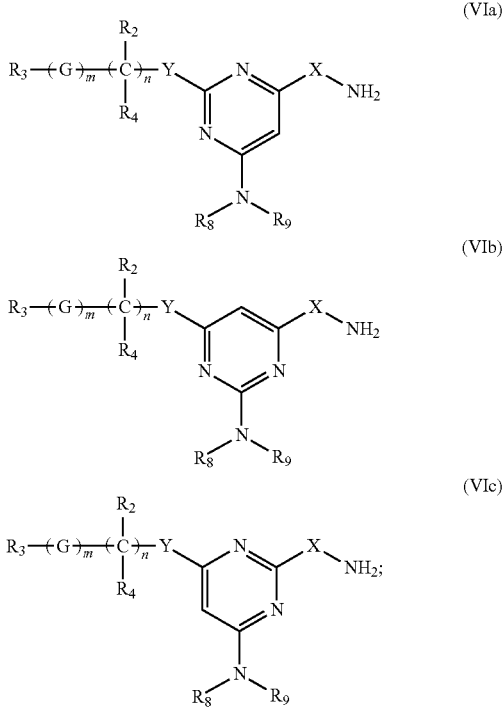

(VIa)
(VIb)
(VIc)

d) adding water to the mixture of isomers represented by formulas (VIa), (VIb), and (VIc), wherein the volume of water added is about 1 to about 4 times the volume of the polar solvent;

e) allowing the compound represented by formula (VIa) to selectively precipitate out of solution at room temperature;

d) collecting the precipitate comprising a compound represented by formula (VIa);

e) heating in the presence of a catalytic amount of an acid the precipitate comprising a compound represented by formula (VIa) and a compound represented by the formula $R_7$—C(O)$R_{10}$, thereby regioselectively forming a compound represented by formula (I).

In one embodiment, the precipitate collected in step d) is a substantially pure regioisomer represented by formula (VIa).

In one embodiment, the 2,4,6-trihalopyrimidine used in the method of the invention is 2,4,6-trichloropyrimidine; the compound represented by $HNR_8R_9$ is morpholine; the compound represented by formula (II) is 2-(2-hydroxyethyl)-pyridine; and the compound represented by $R_7$—C(O)—$R_{10}$ is 3-methylbenzaldehyde.

The invention also provides processes for preparing intermediates that are useful for the preparation of trisubstituted pyrimidine compounds.

The method of the invention reduces the loss of starting material in the formation of undesirable regioisomers. In addition, the method of the invention eliminates the need to separate regioisomers after each reaction step using column chromatography which is time consuming, cumbersome for large scale production (e.g., a large volume of solvent typically must be used to afford a suitable separation of isomers), and typically results in the sacrifice of some of the desired regioisomer. Additional advantages of the method of the invention will be described in detail below.

DETAILED DESCRIPTION OF THE INVENTION

A. Terminology

Unless otherwise specified, the below terms used herein are defined as follows:

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, the term "haloalkoxy" means and alkoxy group in which one or more (including all) the hydrogen radicals are replaced by a halo group, wherein each halo group is independently selected from —F, —Cl, —Br, and —I. Representative haloalkoxy groups include trifluoromethoxy, bromomethoxy, 1,2-dichloroethoxy, 4-iodobutoxy, 2-fluoropentoxy, and the like.

As used herein, the term "alkenyl" means a saturated straight chain or branched non-cyclic hydrocarbon having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2- decenyl, 3-decenyl and the like. Alkenyl groups can be optionally substituted with one or more substituents.

As used herein, the term "alkynyl" means a saturated straight chain or branched non-cyclic hydrocarbon having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be optionally substituted with one or more substituents.

As used herein, the term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

As used herein, the term "cycloalkenyl" means a cyclic non-aromatic alkenyl radical having at least one carbon-carbon double bond in the cyclic system and from 3 to 10 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like. Cycloalkenyl groups can be optionally substituted with one or more substituents.

As used herein, the term an "aromatic ring" or "aryl" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like.

As used herein, the term "alkylene" refers to an alkyl group that has two points of attachment. The term "$(C_1-C_6)$alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyridinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

As used herein, the term "$(C_5)$heteroaryl" means an aromatic heterocyclic ring of 5 members, wherein at least one carbon atom of the ring is replaced with a heteroatom such as, for example, oxygen, sulfur or nitrogen. Representative $(C_5)$ heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "$(C_6)$heteroaryl" means an aromatic heterocyclic ring of 6 members, wherein at least one carbon atom of the ring is replaced with a heteroatom such as, for example, oxygen, nitrogen or sulfur. Representative $(C_6)$ heteroaryls include pyridyl, pyridazinyl, pyrazinyl, triazinyl, tetrazinyl and the like.

As used herein, the term "heteroaralkyl" means a heteroaryl group that is attached to another group by a $(C_1-C_6)$ alkylene. Representative heteroaralkyls include 2-(pyridin-4-yl)-propyl, 2-(thien-3-yl)-ethyl, imidazol-4-yl-methyl and the like.

The term "heterocycle," as used herein, refers collectively to heterocycloalkyl groups and heteroaryl groups.

As used herein, the term "halogen" or "halo" means —F, —Cl, —Br or —I.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —$C(O)NR_{11}R_{12}$, —$NR_{13}C(O)R_{14}$, a halo, —$OR_{13}$, cyano, nitro, a haloalkoxy, —$C(O)R_{13}$, —$NR_{11}R_{12}$, —$SR_{13}$, —$C(O)OR_{13}$, —$OC(O)R_{13}$, —$NR_{13}C(O)NR_{11}R_{12}$, —$OC(O)NR_{11}R_{12}$, —$NR_{13}C(O)OR_{14}$, —$S(O)_rR_{13}$, —$NR_{13}S(O)_rR_{14}$, —$OS(O)_rR_{14}$, $S(O)_rNR_{11}R_{12}$, =O, =S, and =N—$R_{13}$, wherein r is 1 or 2; $R_{11}$ and $R_{12}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or $R_1$ and $R_{12}$ taken together with the nitrogen to which they are attached is optionally substituted heterocycloalkyl or optionally substituted heteroaryl; and $R_{13}$ and $R_{14}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl.

A substituent has a substantially adverse affect on the desired activity of a compound if the compound is about 20% less active with the substituent than without it.

As used herein, the terms "subject", "patient" and "animal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human. In another embodiment, the subject is refractory or non-responsive to current therapies for an inflammatory disorder or an autoimmune disorder (e.g., insulin-dependent diabetes mellitus, multiple sclerosis, rheumatoid arthritis, psoriasis, Crohn's disease, or sepsis).

As used herein, the term "lower" refers to a group having up to four atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

Unless indicated otherwise, the compounds of the invention and intermediates useful in the preparation of compounds of the invention containing reactive functional groups (such as (without limitation) carboxy, hydroxy, thiol, and amino moieties) also include protected derivatives thereof. "Protected derivatives" are those compounds in which a reactive site or sites are blocked with one ore more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein, the term "solvent" refers to a single solvent or a mixture of two or more solvents.

As used herein, the term "compound(s) of this invention" and similar terms refers to a compound of formula (I) or a compound in Table 1, or a pharmaceutically acceptable salt, solvate, clathrate, hydrate, polymorph or prodrug thereof, and also include protected derivatives thereof.

The compounds of the invention may contain one or more chiral centers and, therefore, may exist as enantiomers, or diastereomers. In addition, compounds of the invention may contain one or more double bonds and, therefore, may exist as geometric isomers. According to this invention, the chemical structures depicted herein, including the compounds of this invention, encompass all of the corresponding compounds' enantiomers, diastereomers and geometric isomers, that is, both the stereomerically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

The term "regioselective," as used herein, refers to a chemical reaction in which one regioisomer is obtained preferentially over other possible regioisomers that could be obtained from the reaction. In one embodiment, about 70% by weight of the desired regioisomer is obtained from a regioselective reaction; more preferably, more than about 80% by weight of the desired regioisomer is obtained from a regioselective reaction; even more preferably, more than about 95% by weight of the desired regioisomer is obtained from a regioselective reaction; and most preferably more than about 97% by weight of the desired regioisomer is obtained from a regioselective reaction.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, he term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of formula (I) or Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I) or Table 1 that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

The compounds of the invention are useful for immunosuppression and in the treatment of immune disorders, inflammatory disorders and allergic disorders, as described more fully in U.S. Pat. Nos. 6,693,097, 6,660,733 and U.S. patent application Ser. Nos. 10/305,039, 10/656,671, 10/655,672, and 60/585,124.

"Immunosuppression" refers to impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415-1450, Taylor & Francis, Philadelphia, Pa.).

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the brain in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease, Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

The compounds of this invention can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a compound or a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

As used herein, the term "pharmaceutically acceptable salt," is a salt formed from, for example, an acid and a basic group of one of the compounds of formula (I) or Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of formula (I) or Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more pharmaceutically acceptable solvent molecules to one of the compounds of formula (I) or Table 1. The term solvate includes hydrates (e.g., hemihydrate, monohydrate, dihydrate, trihydrate, tetrahydrate, and the like).

An "effective amount" is the quantity of compound in which a beneficial outcome is achieved when the compound is administered to a subject or alternatively, the quantity of compound that possess a desired activity in-vivo or in-vitro. In the case of inflammatory disorders, allergic disorders and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder or autoimmune disorder, allergic disorders, or the degree of immunosuppression sought. The skilled artisan will be able to determine appropriate dosages depending on these and other factors.

As used herein, the terms "treat", "treatment" and "treating" refer to the reduction or amelioration of the progression, severity and/or duration of an inflammatory disorder, allergic disorder and autoimmune disorder, or the amelioration of one or more symptoms (preferably, one or more discernible symptoms) of an inflammatory disorder, allergic disorder and autoimmune disorder resulting from the administration of one or more therapies (e.g., one or more therapeutic agents such as a compound of the invention).

As used herein, the terms "prevent", "prevention" and "preventing" refer to the reduction in the risk of acquiring or developing an inflammatory disorder, allergic disorder and autoimmune disorder, or the reduction or inhibition of the recurrence, onset or development of one or more symptoms of an inflammatory disorder, allergic disorder and autoimmune disorder.

As used herein, "selectively precipitating a regioisomer" means that the resulting precipitate has a molar ratio of a desired regioisomer to the combination of undesired regioisomers of more than about 7:3; more preferably, more than about 4:1; even more preferably, more than about 9.5:1; and most preferably, more than about 9.7:1.

As used herein, a composition that "substantially" comprises a compound means that the composition contains more than about 70% by weight, more preferably more than about 80% by weight, even more preferably more than about 95% by weight, and most preferably more than about 97% by weight of the compound.

As used herein, a reaction that is "substantially complete" means that the reaction contains more than about 70% by weight of the expected product, more preferably more than about 80% by weight of the expected product, even more preferably more than about 95% by weight of the expected product, and most preferably more than about 97% by weight of the expected product.

A functional group or a protected functional group is "substantially stable" to reaction conditions if the function group or protected functional group is more than about 70%, more preferably more than about 80%, even more preferably more than about 95%, and most preferably more than about 97% unchanged during the reaction.

As used herein, a racemic mixture means about 50% of one enantiomer and about 50% of is corresponding enantiomer relative to a chiral center in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic method Compounds produced by the method of the invention are defined herein by their chemical structures and/or chemical names. Where a compound is referred to by both a chemical structure and a chemical name, and the chemical structure and chemical name conflict, the chemical structure is determinative of the compound's identity.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

B. Process of the Invention

The present invention provides a regioselective process for preparing trisubstituted pyrimidine and processes for preparing intermediates that are useful for the preparation of trisubstituted pyrimidine compounds.

In one embodiment, the present invention provides a method for preparing a mixture of regioisomers (IIIa) and (IIIb) represented by the following formulas:

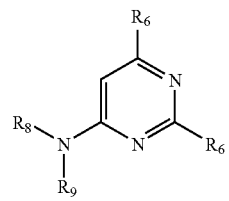

IIIa

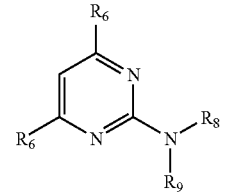

IIIb

In formulas (IIIa) and (IIIb), $R_6$, for each occurrence, is independently F, Cl, Br, or I; and $R_8$ and $R_9$ are defined as in formula (I). The method comprises reacting $HNR_8R_9$ with a 2,4,6-trihalopyrimidine in a solvent to form said regioisomeric mixture of (IIIa) and (IIIb). During the reaction, the amine compound, $HNR_8R_9$, is present in an excess amount compared to the 2,4,6-trihalopyrimidine. Utilization of an excess amount of the amine compound compared to the 2,4,6-trihalopyrimidine surprisingly did not lead to a disubstitution of the pyrimidine with the amine compound, but instead resulted in fewer unwanted side products. Typically, more of regioisomer (IIIa) is formed than regioisomer IIIb. In one embodiment, the ratio of regioisomer (IIIa) to (IIIb) is between about 2.5:1 to about 5:1.

In one embodiment, a mixture of the amine compound and the solvent is prepared and cooled to a temperature in the range of between about −20° C. and about 10° C., then the 2,4,6-trihalopyrimidine is added to the mixture. In one embodiment, between about 0.4 to about 0.6 equivalents of the 2,4,6-trihalopyrimidine is added to the reaction mixture. Preferably, the reaction temperature is maintained in the range of between about −20° C. and about 10° C.

In another embodiment, the 2,4,6-trihalopyrimidine compound is 2,4,6-trichloropyrimidine.

In another embodiment, the amine compound which reacts with the 2,4,6-trihalopyrimidine can be represented by formula V:

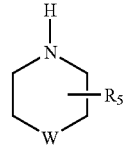

(V)

In formula (V), W is O, S, S(O), S(O)$_2$, NR$^c$, or NC(O)R$^c$; R$_5$ is H or alkyl; and R$^c$ is H, alkyl, aryl, aralkyl, heteroaryl, heteroaralkyl, cycloalkyl, heterocycloalkyl, —C(O)-alkyl, or —S(O)$_2$R$_f$.

In another embodiment, the compound represented by formula (V) is morpholine.

In another embodiment, the 2,4,6-trihalopyrimidine is dissolved in a solvent prior to being added to the mixture of the amine compound in a solvent.

In another embodiment, the solvent that the 2,4,6-trihalopyrimidine compound is dissolved in comprises ethyl acetate, an ether, (e.g., tetrahydrofuran, dioxane, diethyl ether, etc.), an alcohol (e.g., ethanol, isopropanol, etc.), dimethylformamide, dimethylacetamide, acetonitrile, or combinations thereof.

In another embodiment, the amine compound is dissolved in a solvent comprising ethyl acetate, an ether, (e.g., tetrahydrofuran, dioxane, diethyl ether, and the like), an alcohol (e.g., ethanol, isopropanol, etc.), dimethylformamide, dimethylacetamide, acetonitrile, or combinations thereof.

In another embodiment, the solvent used to dissolve the amine compound also comprises water. Inclusion of water in the reaction mixture is advantageous because it causes the regioisomers (IIIa) and (IIIb) to precipitate out of solution, thereby reducing the formation of unwanted side products (e.g., diamino-halopyrimidine).

In another embodiment, the amine compound is in a solution of an alcohol and water. Preferably, the amine compound is in a solution of ethanol and water. More preferably, the ratio of ethanol to water in the reaction mixture after addition of the 2,4,6-trihalopyrimidine is in the range of between about 1:1.5 and about 0.75:1.

In another embodiment, the present invention provides a method for regioselectively preparing a compound represented by the formula (IVa):

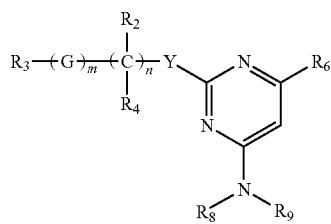
(IVa)

In formula (IVa), G, R$_2$, R$_3$, R$_4$, R$_8$, R$_9$ Y, m, and n are defined as in formula (I); and R$_6$ is defined as in formulas (IIIa) and (IIIb). The method comprising the steps of:

a) preparing a mixture comprising an anhydrous polar solvent, a compound represented by formula (II):

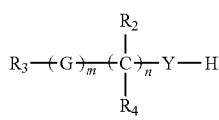
(II)

and regioisomers (IIIa) and (IIIb) represented by the following formulas:

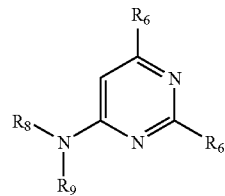
(IIIa)

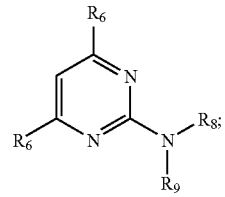
(IIIb)

b) adding a strong base to the mixture formed in step a), thereby forming a mixture of regioisomers represented by formulas (IVa), (IVb), and (IVc):

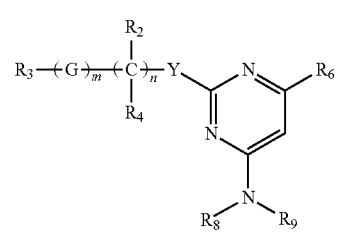
(IVa)

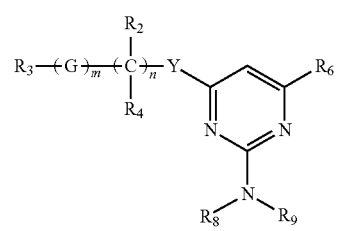
(IVb)

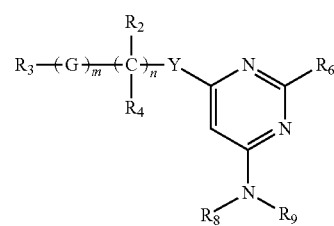
(IVc)

c) adding water to the mixture of regioisomers, thereby selectively precipitating the compound represented by formula (IVa); and d) collecting the precipitate, thereby regioselectively preparing the compound represented by formula (IVa).

In one embodiment, the precipitate collected in step d) comprises at least about 70% of regioisomer (IVa), the desired product. Preferably, the precipitate collected in step d) comprises at least about 80% of regioisomer (IVa).

Since there are two halo groups on regioisomers (IIIa) and (IIIb) that can undergo nucleophilic substitution with the compound represented by formula (II), it is desirable to have an excess of regioisomers (IIIa) and (IIIb) in the reaction mixture compared to the amount of anion formed by contacting a compound represented by formula (II) with a base. One method for maintaining an excess of the regioisomers compared to the anion is to form the anion of the compound of formula (II) by mixing it with the base separately, then add the anion mixture to a solution containing regioisomers (IIIa) and (IIIb). However, the present inventors found that the compound represented by formula (II) forms elimination products in the presence of a base so that this method produces unwanted side products.

Another method for maintaining an excess of regioisomers (IIIa) and (IIIb) compared with the anion would be to form a mixture of regioisomers (IIIa) and (IIIb) and the base and slowly add the compound represented by formula (II) to the mixture so that as the compound of formula (II) was added to the mixture of regioisomers it would form the anion and immediately react with one of the regioisomers. However, this method also formed unwanted side products because regioisomers (IIIa) and (IIIb) can react with the base to form dechlorinated products.

To overcome these difficulties and form the desired product with fewer impurities, the present inventors determined that slowly adding the base to a mixture of a compound of formula (II) and regioisomers (IIIa) and (IIIb) maintained the excess of regioisomers (IIIa) and (IIIb) compared to the amount of anion formed and reduced the amount of unwanted side products formed. Therefore, it is desirable to add the base to a solution of regioisomer (IIIa) and (IIIb) and the compound represented by formula (II) dropwise if the base is a liquid and portionwise if the base is a solid. In one embodiment, the base is added in at least 2, 3, 4, 5, 6, 7, 8, 9, or 10 separate portions. In another embodiment, the base is added at a rate which will maintain the reaction temperature below 10° C. Preferably, the reaction temperature is maintained in the range of between about −20° C. and about 10° C.

In one embodiment, the base is a metal hydride or an organometallic base. In another embodiment, the base is selected from the group consisting of sodium hydride, potassium hydride, potassium tertiary butoxide, butyl lithium (BuLi), phenyl lithium, methyl lithium, and combinations thereof. In one embodiment, the base is sodium hydride or potassium hydride. Preferably, the sodium hydride or the potassium hydride is dispersed in a mineral oil which allows for safer handling. Typically, the amount of base added to the reaction mixture is less than or equal to about 1.5 molar equivalents in relation to the total molar amount of regioisomers (IIIa) and (IIIb) in the reaction mixture. Preferably, the amount of base added is in the range of between about 1 molar equivalent and about 1.5 molar equivalents in relation to the total molar amount of regioisomers (IIIa) and (IIIb).

In one embodiment, the reaction of a compound of formula (II) and regioisomers (IIIa) and (IIIb) is carried out in a polar solvent. Preferably, the polar solvent is a water miscible polar organic solvent. In one embodiment, the reaction is carried out in a solvent selected from the group consisting of dimethylacetamide (DMA), N-methylpyrrolidine (NMP), tetrahydrofuran (THF), dioxane, hexamethylphosphoramide (HMPA), or mixtures thereof.

The reaction forms three regioisomer (IVa), (IVb) and (IVc) in which the desired regioisomer is (IVa). After completion of the reaction, water is added to the reaction mixture to selectively precipitate out the desired regioisomer while leaving the majority of the undesirable regioisomers (IVb) and (IVc) in solution. In one embodiment, the amount of water added to the reaction mixture is in the range of between about 0.75 volume equivalents and about 1.25 volume equivalents in relation to the volume of the polar solvent. The ratio of regioisomer (IVa) to the combination of regioisomers (IVb) and (IVc) obtained by this precipitation method is in the range of between about 8:1 and about 4:1 with a typical precipitation yielding a ratio of regioisomer (IVa) to the combination of regioisomers (IVb) and (IVc) of about 6:1.

As disclosed above, the base which is used to form the anion of a compound of formula (II) may be dispersed in a mineral oil. Dispersion in a mineral oil makes many metal hydride or an organometallic bases easier and safer to handle because it reduces their flammability when exposed to air. However, mineral oil in the reaction mixture is an impurity that must be removed from the final product. In order to remove the mineral oil from the reaction mixture, a hydrocarbon solvent is added to the reaction mixture after the reaction is complete and the mixture to stir for a period of time. Typically, for every 1 g of regioisomers (IIIa) and (IIIb) together in the reaction mixture to start with, about 0.5 g of hydrocarbon solvent is added to the reaction mixture once the reaction is complete. In one embodiment, the hydrocarbon solvent used is selected from the group consisting of heptane, hexanes, cyclohexane, petroleum ether, pentane, or combinations thereof. In a preferred embodiment, the hydrocarbon solvent is heptane or hexane. The mixture is then allowed to settle, and the oil dissolved in the hydrocarbon solvent collects in a layer at the top of the mixture and can be readily removed. Surprisingly, stirring the reaction mixture with a hydrocarbon solvent for at least one hour before precipitation of the product with water, typically increases the ratio of the desired regioisomer (IVa) to the combination of regioisomers (IVb) and (IVc) from about 6:1 to in the range of between about 8:1 and about 12:1. Generally, the ratio of the desired regioisomer (IVa) to the combination of regioisomers (IVb) and (IVc) in the precipitate is about 10:1 after this procedure. In one embodiment, the reaction mixture and hydrocarbon solvent is allowed to stir for a period of time in the range of between about 1 hour and about 2 hours. Generally, if the reaction mixture is stirred for a period of time shorter than an hour with the hydrocarbon solvent, the ratio of the desired regioisomer (IVa) to the combination of regioisomers (IVb) and (IVc) in the precipitate decreases.

After the product is precipitated out of solution and collected, the ratio of the desired regioisomer (IVa) to the combination of regioisomers (IVb) and (IVc) in the precipitate can be further improved by washing the precipitate with a hydrocarbon solvent. One method of washing the precipitate with a hydrocarbon solvent is to pour the hydrocarbon solvent over the precipitate which has been collected by filtration and allow the hydrocarbon solvent to filter off. In one embodiment, the precipitate is washed with a hydrocarbon solvent selected from the group consisting of heptane, hexanes, cyclohexane, petroleum ether, pentane, and combinations thereof. Washing the precipitate with a hydrocarbon solvent typically improved the ratio of the desired regioisomer (IVa) to the combination of regioisomers (IVb) and (IVc) from about 10:1 to in the range of between about 40:1 and about 60:1.

In one embodiment, regioisomers (IIIa) and (IIIb) are prepared by reacting a compound represented by the formula $HNR_8R_9$ with a 2,4,6-trihalopyrimidine as disclosed above. In a preferred embodiment, the 2,4,6-trihalopyrimidine is 2,4,6-trichloropyrimidine, the compound represented by formula $HNR_8R_9$ is morpholine and the compound represented by formula (II) is 2-(2-hydroxyethyl)-pyridine.

In another embodiment, the present invention provides a method for regioselectively preparing a compound represented by the formula (VIa):

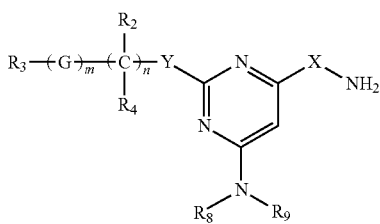

(VIa)

In formula (VIa), X, G, $R_2$, $R_3$, $R_4$, $R_8$, $R_9$, Y, m and n are defined as in formula (I). The method comprises the steps of:

a) heating a suspension comprising hydrazine, $NH_2$—$NHR^e$, $NH_2$—$NHR^i$, HO—$NHR^i$, or HS—$NHR^i$, wherein $R^i$ is an amine protecting group and $R^i$ is an alkyl; and a regioisomeric mixture in a polar solvent, wherein the regioisomeric mixture comprises compounds represented by formulas (IVa), (IVb) and (IVc):

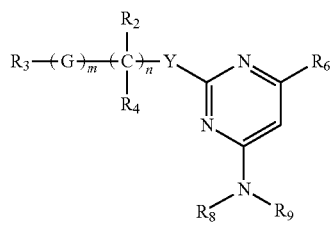

(IVa)

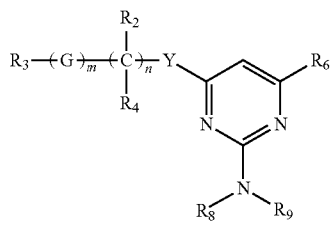

(IVb)

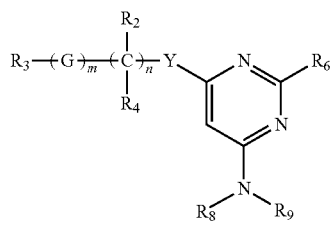

(IVc)

wherein $R_6$ is F, Cl, Br, or I, thereby forming a second regioisomeric mixture comprising regioisomers represented by formulas (VIa), (VIb) and (VIc):

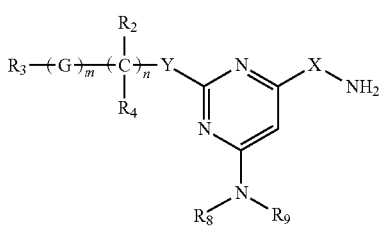

(VIa)

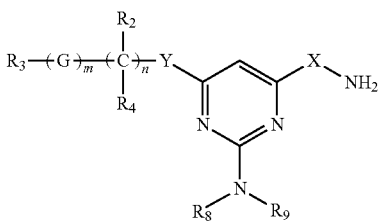

(VIb)

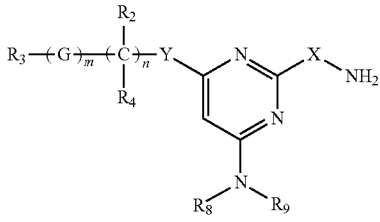

(VIc)

b) adding water to the mixture of regioisomers, wherein the volume of water added is about 1 to about 4 times the volume of the polar solvent;

c) allowing the compound represented by formula (VIa) to selectively precipitate out of solution at room temperature; and d) collecting the precipitate, thereby regioselectively preparing the compound represented by formula (VIa).

The reaction is typically carried out in a polar organic solvent, such as an ether (e.g., tetrahydrofuran (THF), a dioxane, etc.), dimethylacetamide (DMA), N-methylpyrrolidine (NMP), hexamethylphosphoramide (HMPA), or mixtures thereof. Preferably, the reaction is carried out in dioxane. Typically, when the reaction is carried out in dioxane, the reaction is heated to between about 80° C. and about 105° C.

In one embodiment, about 3.5 molar equivalents of an amine compound selected from the group consisting of hydrazine, $NH_2$—$NHR^e$, $NH_2$—$NHR^i$, HO—$NHR^i$, or HS—$NHR^i$ in relation to the total molar amount of regioisomers (IVa), (IVb) and (IVc) is added to the reaction mixtures, and the reaction is typically allowed to proceed for a period of time in the range of between about 3 hours to about 6 hours. In a one embodiment, the amine compound added to the reaction mixture is hydrazine, preferably hydrazine-hydrate. It is preferable to use hydrazine-hydrate instead of anhydrous hydrazine because it is less flammable and explosive than anhydrous hydrazine. When hydrazine-hydrate is used instead of anhydrous hydrazine in the above reaction the reaction time is typically increased by about an hour to 1.5 hours. In addition, when the reaction is carried out on large scale, it is occasionally necessary to add an addition amount of the amine compound to the reaction mixture after the reaction has proceeded for about 3 hours to about 4 hours. Typically, the additional amount of amine compound added is in the range of between about 0.2 molar equivalents to about 0.6 molar equivalents in relation to the total molar amount of regioisomers (IVa), (IVb) and (IVc).

Since regioisomer (VIa) is the desired product, it is desirable to find a solvent mixture that will precipitate out most of regioisomer (VIa) and allow most of the undesirable regioisomers (IVb) and (IVc) to remain in solution. To achieve this, water is added to the reaction mixture after the reaction is substantially completion. Typically, the volume of water added to the reaction mixture is between about 1 to about 4 times the volume of the polar solvent in which the reaction is carried out. When the ratio of regioisomer (IVa) to the combination of regioisomers (IVb) and (IVc) in the starting materials is less than about 6:1, it is desirable to allow the product to precipitate out of solution for only about 2 hours to about 12 hours. After about 12 hours, more of the undesirable products will also precipitate out of solution depending on how much of the undesirable regioisomer (IVb) and (IVc) are present in the starting material. However, if the starting material had a ratio higher than 6:1 of the desired regioisomer (IVa) to the combination of regioisomers (IVb) and (IVc), the product can be allowed to precipitate out of solution for more than 12 hour without substantially decreasing the amount of the desired regioisomer (VIa) in the product. Allowing a longer precipitation time can increase the yield of the product. In one embodiment, the precipitate collected in step d) comprises at least 80% of the desired product, regioisomer (VIa). Preferably, the precipitate collected in step d) comprises at least 90% of the desired product, regioisomer (VIa).

The precipitate collected in step d) may be further purified by recrystallizing the product. In one embodiment, the recrystallization solvent is an alcohol, such as ethanol.

In one embodiment, the product, regioisomer (VIa), can be further reacted with an aldehyde or ketone represented by the formula $R_7$—C(O)$R_{10}$, in the presence of a catalytic amount of an acid, wherein $R_7$ and $R_{10}$ are defined as in formula (I), to form a compound represented by formula (I):

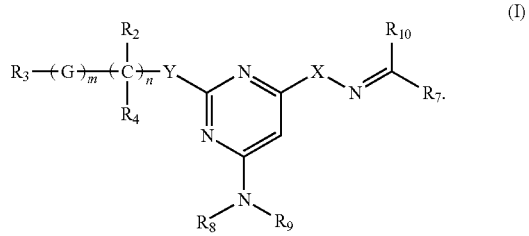
(I)

Typically, the reaction of regioisomer (VIa) and the aldehyde or ketone is carried out in a polar solvent. In one embodiment, the reaction solvent is selected from the group consisting of ethyl acetate, an ether (e.g., tetrahydrofuran, dioxane, diethyl ether, etc.), an alcohol (e.g., ethanol, isopropanol, etc.), dimethylformamide, dimethylacetamide, acetonitrile, or combinations thereof. In a preferred embodiment, the reaction is carried out in an alcohol, such as ethanol. In another a preferred embodiment, the reaction is carried out in ethyl acetate.

The acid used to catalyze the reaction can be an organic acid, such as a carboxylic acid (e.g., acetic acid, formic acid, benzoic acid, etc.), halogenated carboxylic acids (e.g., trichloroacetic acid), alkylsulfonic acids (e.g., methanesulfonic acid), arylsulfonic acids (e.g., benzenesulfonic acid), haloalkyl sulfonic acids (e.g., trifluoromethanesulfonic acid), di- or tri-nitrophenolic acids. The acid used to catalyze the reaction may also be an inorganic acid, such as hydrochloric acid, hydrobromic acid, and the like. In one embodiment, the acid catalyst is acetic acid.

In one embodiment, regioisomer (VIa) and an aldehyde or ketone can be heated to facilitate the reaction. The amount of heat applied is dependant on the reactivity of the starting materials. For example, ketones are typically less reactive than aldehydes and may require a higher temperature in order to react with regioisomer (VIa). In one embodiment, the reaction temperature is in the range of between about 50° C. and about 100° C.

In one embodiment, the compound represented by the formula $R_7$—C(O)$R_{10}$ is an aldehyde, such as 3-methylbenzaldehyde, 1H-indole-3-carbaldehyde, 3-methyl-benzaldehyde, 3-ethyl-benzaldehyde, 3-iodobenzaldehyde, 3-fluorobenzaldehyde, 3-chlorobenzaldehyde, 3-bromobenzaldehyde, 3-formyl-benzoic acid methyl ester, 3-formyl-N-methyl benzamide, and 3-hydroxymethyl-benzaldehyde. In a preferred embodiment, the compound represented by the formula $R_7$—C(O)$R_{10}$ is 3-methylbenzaldehyde.

Typically, the compound represented by formula (I) will precipitate out of the reaction mixture and can be collected by filtration. Since the method of the invention allows regioisomer (VIa) to be prepared with a high degree of regioselectivity, the precipitated compound represented by formula (I) typically has a purity of at least about 80%, and more typically at least about 90%, without any additional purification. If a higher purity is desired the compound of formula (I) can be recrystallized from, for example, ethanol.

The processes described herein can include the use of appropriate protecting groups at any reactive site when necessary or advantageous. For instance, reactive sites of the intermediates and/or starting materials described herein can be blocked with one or more protecting groups. Suitable protecting groups for carboxy moieties include benzyl, tert-butyl, and the like. Suitable protecting groups for amino and amido groups include acetyl, tert-butoxy-C(O)—, benzyloxy-C(O)—, and the like. Suitable protecting groups for hydroxy groups include benzyl and the like. Other suitable protecting groups are well known to those of ordinary skill in the art and include those found in T. W. Greene, Protecting Groups in Organic Synthesis, John Wiley & Sons, Inc. 1981.

C. Compounds of the Invention

The present invention encompasses processes useful for preparing compounds represented by formulas (I), (IIIa), (IIIb), (IVa), (IVb), (IVc), (VIa), (VIb), (VIc) and those set forth in Table 1.

In one embodiment, the method of the invention is useful for preparing compounds represented by formula (I):

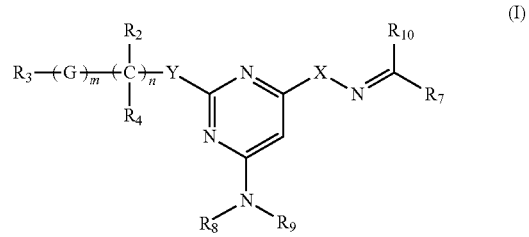
(I)

or a salt, solvate, clathrate, or prodrug thereof, wherein:
X is —, —S—, —NH—, or —NR$^e$—;
G is —O—, —C(O)NHNH—, —NHNHC(O)—, —C(O)NR$^f$NR$^g$—, —NR$^f$NR$^g$C(O)—, —CH=N—NH—, —NH—N=CH—CR$^g$=N—NR$^f$—, —NR$^f$—N=CR$^g$—, —NHNH—, —NR$^f$NR$^g$—, —NHO— —O—NH—, —O—NR$^c$—, —NR$^c$—O—, —CH=N—O—, —O—N=CH—, —CR$^f$=N—O—, —O—N=CR$^f$—, —O—C(O)—NH—, —O—C(O)—NR$^f$—, —O—C(S)—NH—, —NH—C(S)—O—, —O—C(S)—NR$^f$—, —NR$^-$C(S)—O—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R$^c$)—NH—, —NH—C(O)—NH—, —NR$^c$—C(O)—NR$^c$—, —NH—C(S)—NH— and —NR$^c$—C(S)—

$NR^c$—, —NH—S(O)$_2$—NH—, —NRC—S(O)$_2$—NR$^c$—, —N(R$^c$)—S(O)$_2$—O—, —P(O)(R$^c$)—, —P(O)(R$^c$)—O—, —P(O)(R$^c$)—NR$^c$—, -Cyclyl-, -Heterocycloalkyl-, -Aryl-, -Heteroaryl-, -Heteroaralkyl-, -Heteroaryl-NH—, -Heteroaryl-S—, -Heteroaralkyl-O—, —C(N—CN)—NH—, —Si(OH)$_2$—, —B(OH)—, —C(NH)—NR$^c$—, —N(R$^c$)—CH$_2$—C(O)—, —C(O)—ON(R$^c$)—, —C(O)—N(R$^c$)O—, —C(S)—ON(R$^c$)—, —C(S)—N(R$^c$)O—, —C(N(R$^d$))—ON(R$^c$)—, —C(N(R$^d$))—NR$^c$O—, —OS(O)$_2$—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)$_2$O—, —N(R$^c$)N(R$^c$)C(S)O—, —N(R$^c$)N(R$^c$)C(N(R$^d$))O—, —OP(O)$_2$O—, —N(R$^c$)P(O)$_2$O—, —OP(O)$_2$N(R$^c$)—, —N(R$^c$)P(O)$_2$N(R$^c$)—, —P(O)$_2$O—, —P(O)$_2$N(R$^c$)—, —N(R$^c$)P(O)$_2$—, —OP(O)$_2$—, —O-alkyl-heterocycloalkyl-N(R$^c$)—, —N(R$^c$)CHR$^d$C(O)N(R$^c$)CHR$^d$C(O)—, —N(R$^c$)CHR$^d$C(O)—, —N(R$^c$)C(O)CHR$^d$—, or —C(O)N(R$^c$)CHR$^d$C(O)—; wherein R$^f$, R$^g$ and R$^h$, for each occurrence is H, alkyl, aryl, heteroaryl, aralkyl, cycloalkyl, or heterocycloalkyl;

$R_2$ and $R_4$, for each occurrence, are, independently, R$^c$, alkenyl, alkynyl, halogen, nitro, cyano, isothionitro, SR$^c$, or OR$^c$; or $R_2$ and $R_4$, taken together with the carbon to which they are attached, are a carbonyl;

$R_3$ is R$^c$, alkenyl, alkynyl, —OR$^c$, —OC(O)R$^c$, —SO$_2$R$^c$, —S(O)R$^c$, —S(O)$_2$NR$^c$R$^d$, —SR$^c$, —NR$^c$R$^d$, —NR$^c$COR$^d$, —NR$^c$C(O)R$^d$, —NR$^c$C(O)OR$^d$, —NR$^c$C(O)NR$^c$R$^d$, —NR$^c$SO$_2$R$^d$, —C(O)R$^c$, —C(O)OR$^c$, —C(O)NR$^c$R$^d$, —P(O)OR$^c$OR$^d$, or S(O)$_2$NR$^c$R$^d$;

$R_7$ is an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; and $R_8$ and $R_9$ are each, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or $R_8$ and $R_9$ taken together with the nitrogen to which they are attached are an optionally substituted heterocycloalkyl or an optionally substituted heteroaryl;

$R_{10}$ is H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl;

n is 0, 1, 2, 3, 4, 5, or 6;

m is 0 or 1;

Y is O, S, or NR$^c$;

R$^c$ and R$^d$, for each occurrence, are, independently, H, alkyl, aryl, aralkyl, heteroaryl, heteroaralkyl, cycloalkyl, heterocycloalkyl, —C(O)-alkyl, or —S(O)$_2$R$_f$; and R$^e$ is a lower alkyl.

A compound of formula (I) or a pharmaceutically acceptable salt, solvate, clathrate, hydrate, polymorph or prodrug thereof is particularly useful for treating or preventing immune disorders, inflammatory disorders and allergic disorders.

In one embodiment, in compounds represented by formula (I) $R_3$ is an optionally substituted pyridinyl, such as pyridine-2-yl, pyridine-3-yl, and I-oxo-pyridine-2-yl.

In another embodiment, in compounds represented by formula (I), $R_3$ is pyrid-2-on-1-yl.

In another embodiment, in compounds represented by formula (I), $R_3$ is an optionally substituted phenyl, such as phenyl and 3,4-dimethoxy-phenyl.

In another embodiment, in compounds represented by formula (I), $R_3$ is hydroxy.

In another embodiment, in compounds represented by formula (I), $R_3$ is [1,3]dioxin-2-yl.

In another embodiment, in compounds represented by formula (I), $R_3$ is an alkoxy, such as methoxy.

In another embodiment, in compounds represented by formula (I), $R_3$ is 2,2-dimethyl-[1,3]dioxolan-4-yl.

In another embodiment, in compounds represented by formula (I), $R_3$ is an alkyl.

In another embodiment, in compounds represented by formula (I), $R_3$ is a group represented by —C(O)OR$^c$, such as —C(O)OCH$_2$CH$_3$.

In another embodiment, in compounds represented by formula (I) $R_7$ is an optionally substituted indolyl, such as 1H-indol-3-yl and 2,3-dimethoxy-indol-5-yl.

In another embodiment, in compounds represented by formula (I), $R_7$ is an optionally substituted phenyl, such as phenyl, 3-methylphenyl, 3-ethylphenyl, 3-iodophenyl, 3-fluorophenyl, 3-chlorophenyl, 3-bromophenyl, 3-iodophenyl, 3-methylcarbonyl-phenyl, 3-methylcarbamoyl-phenyl, and 3-hydroxymethyl-phenyl.

In another embodiment, in compounds represented by formula (I), $R_{10}$ is —H.

In another embodiment, in compounds represented by formula (I), $R_{10}$ is methyl.

In another embodiment, in compounds represented by formula (I), n is 1 or 2 and m is 0.

In another embodiment, in compounds represented by formula (I), n is 1 or 2 and m is 1.

In another embodiment, in compounds represented by formula (I), Y is —O—.

In another embodiment, in compounds represented by formula (I), G is —O— and m is 1.

In another embodiment, in compounds represented by formula (I), X is —NH—.

In another embodiment, in compounds represented by formula (I), X is —O—.

In another embodiment, in compounds represented by formula (I), —NR$_8$R$_9$ is an optionally substituted heterocycloalkyl ring, such as morpholine.

In another embodiment, in compounds represented by formula (I), $R_8$ and $R_9$ are each independently an optionally substituted alkyl, such as methyl, ethyl, n-propyl, isopropyl, and the like.

In another embodiment, in compounds represented by formula (I), $R_8$ and $R_9$ are both methyl.

In another embodiment, in compounds represented by formula (I), $R_2$ and $R_4$ are both —H, and n is an integer from 1 to 6.

In another embodiment, in compounds represented by formula (I), $R_2$ and $R_4$ are both —H, and n is an integer from 1 to 2.

In another embodiment, in compounds represented by formula (I), $R_2$ and $R_4$ are —H, n is an integer from 1 to 2, and Y is —O—.

In another embodiment, the compound represented by formula (I) is 2-[2-(Pyridin-2-yl)-ethoxy]4-[N'-(3-methyl-benzilidene)-hydrazino]-6-(morpholin-4-yl)-pyrimidine.

In another embodiment, the method of the invention is useful for preparing an isomeric mixture of compounds represented by formulas (IIIa) and (IIIb):

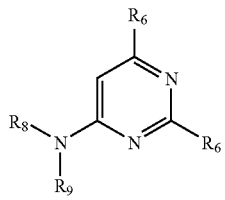

(IIIa)

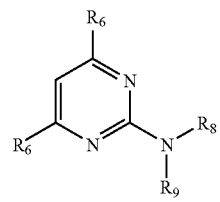

(IIIb)

wherein:

$R_6$, for each occurrence, are independently, —F, —Cl, —Br, or —I; and $R_8$ and $R_9$ are each, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or $R_8$ and $R_9$ taken together with the nitrogen to which they are attached are an optionally substituted heterocycloalkyl or an optionally substituted heteroaryl.

Compounds represented by formula (IIIa) or regioisomeric mixtures that include compounds represented by formula (IIIa) are useful in preparing compounds represented by formula (I), or a pharmaceutically acceptable salt, solvate, clathrate, hydrate, polymorph or prodrug thereof.

In one embodiment, in compounds represented by formulas (IIIa) and/or (IIIb), all $R_6$ groups are —Cl.

In another embodiment, in compounds represented by formulas (IIIa) and/or (IIIb), —$NR_8R_9$ is an optionally substituted heterocycloalkyl, such as morpholine.

In another embodiment, in compounds represented by formulas (IIIa) and/or (IIIb), $R_8$ and $R_9$ are each independently an optionally substituted alkyl, such as methyl, ethyl, n-propyl, isopropyl, and the like.

In another embodiment, in compounds represented by formulas (IIIa) and/or (IIIb), $R_8$ and $R_9$ are both methyl.

In another embodiment, the compound represented by formula (IIIa) is 2,4-dichloro-6-(morpholin-4-yl)-pyrimidine.

In another embodiment, the method of the invention is useful for preparing compounds represented by formulas (IVa), (IVb) and (IVc):

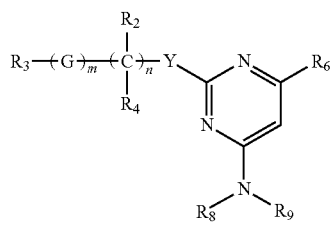

(IVa)

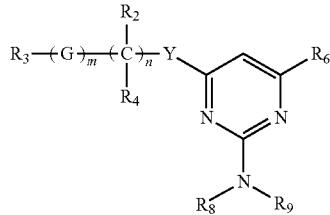

(IVb)

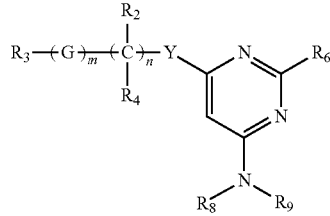

(IVc)

wherein:

G is —O—, —C(O)NHNH—, —NHNHC(O)—, —C(O)NR$^f$NR$^g$—, —NR$^f$NR$^g$C(O)—, —CH=N—NH—, —NH—N=CH—CR$^g$=N—NR$^f$—, —NR$^f$—N=CR$^g$—, —NHNH—, —NR$^f$NR$^g$—, —NHO— —O—NH—, —O—NR$^c$—, —NR$^c$—O—, —CH=N—O—, —O—N=CH—, —CR$^f$=N—O—, —O—N=CR$^f$—, —O—C(O)—NH—, —O—C(O)—NR$^f$—, —O—C(S)—NH—, —NH—C(S)—O—, —O—C(S)—NR$^f$—, —NR$^-$C(S)—O—, —NH—C(NH)—NH—, —NR$^c$—C(NH)—NH—, —N—C(NR$^c$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R)—NH—, —NH—C(O)—NH—, —NR$^c$—C(O)—NR$^c$—, —NH—C(S)—NH— and —NR$^c$—C(S)—NR$^c$—, —NH—S(O)$_2$—NH—, —NR$^c$—S(O)$_2$—NR$^c$—, —N(R$^c$)—S(O)$_2$—O—, —P(O)(R$^c$)—, —P(O)(R$^c$)—O—, —P(O)(R$^c$)—NR$^c$—, -Cyclyl-, -Heterocycloalkyl-, -Aryl-, -Heteroaryl-, -Heteroaralkyl-, -Heteroaryl-NH—, -Heteroaryl-S—, -Heteroaralkyl-O—, —C(N—CN)—NH—, —Si(OH)$_2$—, —B(OH)—, —C(NH)—NR$^c$—, —N(R$^c$)—CH$_2$—C(O)—, —C(O)—ON(R$^c$)—, —C(O)—N(R$^c$)O—, —C(S)—ON(R$^c$)—, —C(S)—N(R$^c$)O—, —C(N(R$^d$))—ON(R$^c$)—, —C(N(R$^d$))—NR$^c$O—, —OS(O)$_2$—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)$_2$O—, —N(R$^c$)N(R$^c$)C(S)O—, —N(R$^c$)N(R$^c$)C(N(R$^d$))O—, —OP(O)$_2$O—, —N(R$^c$)P(O)$_2$O—, —OP(O)$_2$N(R$^c$)—, —N(R$^c$)P(O)$_2$N(R$^c$)—, —P(O)$_2$O—, —P(O)$_2$N(R$^c$)—, —N(R$^c$)P(O)$_2$—, —OP(O)$_2$, —O-alkyl-heterocycloalkyl-N(R$^c$)—, —N(R$^c$)CHR$^d$C(O)N(R$^c$)CHR$^d$C(O)—, —N(R$^c$)CHR$^d$C(O)—, —N(R$^c$)C(O)CHR$^d$, or —C(O)N(R$^c$)CHR$^d$C(O)—; wherein R$^f$, R$^g$ and R$^h$, for each occurrence is H, alkyl, aryl, heteroaryl, aralkyl, cycloalkyl, or heterocycloalkyl;

$R_2$ and $R_4$, for each occurrence, are, independently, R$^c$, alkenyl, alkynyl, halogen, nitro, cyano, isothionitro, SR$^c$, or OR$^c$; or $R_2$ and $R_4$, taken together with the carbon to which they are attached, are a carbonyl;

$R_3$ is R$^c$, alkenyl, alkynyl, —OR$^c$, —OC(O)R$^c$, —SO$_2$R$^c$, —S(O)R$^c$, —S(O)$_2$NR$^c$R$^d$, —SR$^c$, —NR$^c$R$^d$, —NR$^c$COR$^d$, —NR$^c$C(O)R$^d$, NR$^c$C(O)OR$^d$, —NR$^c$C(O)NR$^c$R$^d$, —NR$^c$SO$_2$R$^d$, —C(O)R$^c$, —C(O)OR$^c$, —C(O)NR$^c$R$^d$, —P(O)OR$^c$OR$^d$, or —S(O)$_2$NR$^c$R$^d$;

$R_8$ and $R_9$ are each, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteralkyl; or $R_9$ and $R_9$ taken together with the nitrogen to which they are attached are an optionally substituted heterocycloalkyl or an optionally substituted heteroaryl;

n is 0, 1, 2, 3, 4, 5, or 6;

m is 0 or 1;

Y is O, S, or $NR^c$; and $R^c$ and $R^d$, for each occurrence, are, independently, H, alkyl, aryl, aralkyl, heteroaryl, heteroaralkyl, cycloalkyl, heterocycloalkyl, —C(O)-alkyl, or —S(O)$_2R_f$.

Compounds represented by formula (IVa) or regioisomeric mixtures that include compounds represented by formula (IVa) are useful in preparing compounds represented by formula (I), or a pharmaceutically acceptable salt, solvate, clathrate, hydrate, polymorph or prodrug thereof.

In one embodiment, in compounds represented by formulas (IVa), (IVb) and/or (IVc), $R_3$ is an optionally substituted pyridinyl, such as pyridine-2-yl, pyridine-3-yl, and 1-oxo-pyridine-2-yl.

In another embodiment, in compounds represented by formulas (IVa), (IVb) and/or (IVc), $R_3$ is pyrid-2-on-1-yl.

In another embodiment, in compounds represented by formulas (IVa), (IVb) and/or (IVc), $R_3$ is an optionally substituted phenyl, such as phenyl and 3,4-dimethoxy-phenyl.

In another embodiment, in compounds represented by formulas (IVa), (IVb) and/or (IVc), $R_3$ is hydroxyl or a protected hydroxyl group.

In another embodiment, in compounds represented by formulas (IVa), (IVb) and/or (IVc), $R_3$ is [1,3]dioxin-2-yl.

In another embodiment, in compounds represented by formulas (IVa), (IVb) and/or (IVc), $R_3$ is an alkoxy, such as methoxy.

In another embodiment, in compounds represented by formulas (IVa), (IVb) and/or (IVc), $R_3$ is 2,2-dimethyl-[1,3]dioxolan-4-yl.

In another embodiment, in compounds represented by formulas (IVa), (IVb) and/or (IVc), $R_3$ is an alkyl.

In another embodiment, in compounds represented by formulas (IVa), (IVb) and/or (IVc), $R_3$ is a group represented by —C(O)O$R^c$, such as —C(O)OCH$_2$CH$_3$.

In one embodiment, in compounds represented by formulas (IVa), (IVb) and/or (IVc), all $R_6$ groups are —Cl.

In another embodiment, in compounds represented by formulas (IVa), (IVb) and/or (IVc), n is 1 or 2 and m is 0.

In another embodiment, in compounds represented by formulas (IVa), (IVb) and/or (IVc), n is 1 or 2 and m is 1.

In another embodiment, in compounds represented by formulas (IVa), (IVb) and/or (IVc), Y is —O—.

In another embodiment, in compounds represented by formulas (IVa), (IVb) and/or (IVc), G is —O— and m is 1.

In another embodiment, in compounds represented by formulas (IVa), (IVb) and/or (IVc), —NR$_8$R$_9$ is an optionally substituted heterocycloalkyl ring, such as morpholine.

In another embodiment, in compounds represented by formulas (IVa), (IVb) and/or (IVc), $R_8$ and $R_9$ are each independently an optionally substituted alkyl, such as methyl, ethyl, n-propyl, isopropyl, and the like.

In another embodiment, in compounds represented by formulas (IVa), (IVb) and/or (IVc), $R_8$ and $R_9$ are both methyl.

In another embodiment, in compounds represented by formulas (IVa), (IVb) and/or (IVc), $R_2$ and $R_4$ are both —H, and n is an integer from 1 to 6.

In another embodiment, in compounds represented by formulas (IVa), (IVb) and/or (IVc), $R_2$ and $R_4$ are both —H, and n is an integer from 1 to 2.

In another embodiment, in compounds represented by formulas (IVa), (IVb) and/or (IVc), $R_2$ and $R_4$ are —H, n is an integer from 1 to 2, and Y is —O—.

In another embodiment, the compound represented by formula (IVa) is 2-(2-pyridin-2-yl-ethoxy)-4-chloro-6-(morpholin-4-yl)-pyrimidine.

In another embodiment, the method of the invention is useful for preparing compounds represented by formulas (VIa), (VIb), and (VIc):

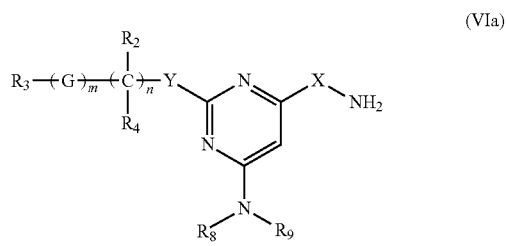

(VIa)

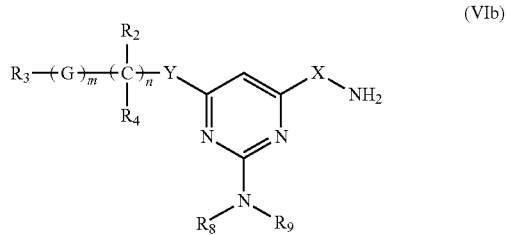

(VIb)

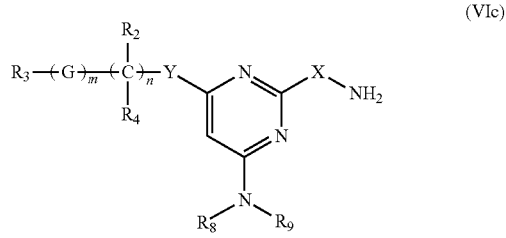

(VIc)

wherein:

X is —O—, —S—, —NH—, or —NR$^e$—;

G is —O—, —C(O)NHNH—, —NHNHC(O)—, —C(O)NR$^f$NR$^g$—, —NR$^f$NR$^g$C(O)—, —CH═N—NH—, —NH—N═CH—CR$^g$═N—NR$^f$—, —NR$^f$—N═CR$^g$—, —NHNH—, —NR$^f$NR$^g$—, —NHO—, —O—NH—, —O—NR$^c$—, —NR$^c$—O—, —CH═N—O—, —O—N═CH—, —CR$^f$═N—O—, —O—N═CR$^f$—, —O—C(O)—NH—, —O—C(O)—NR$^f$—, —O—C(S)—NH—, —NH—C(S)—O—, —O—C(S)—NR$^f$—, —NR$^c$C(S)—O—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R$^c$)—NH—, —NH—C(O)—NH—, —NR$^c$—C(O)—NR$^c$—, —NH—C(S)—NH— and —NR$^c$—C(S)—NR$^c$—, —NH—S(O)$_2$—NH—, —NR$^c$—S(O)$_2$—NR$^c$—, —N(R$^c$)—S(O)$_2$—O—, —P(O)(R$^c$)—, —P(O)(R$^c$)—O—, —P(O)(R$^c$)—NR$^c$—, -Cyclyl-, -Heterocycloalkyl-, -Aryl-, -Heteroaryl-, -Heteroaralkyl-, -Heteroaryl-NH—, -Heteroaryl-S—, -Heteroaralkyl-O—, —C(N═CN)—NH—, —Si(OH)$_2$—, —B(OH)—, —C(NH)—NR$^c$—, —N(R$^c$)CH$_2$—C(O)—, —C(O)—ON(R$^c$)—, —C(O)—N(R$^c$)O—, —C(S)—ON(R$^c$)—, —C(S)—N(R$^c$)O—, —C(N(R$^d$))—

ON(R$^c$)—, —C(N(R$^d$))—NR$^c$O—, —OS(O)$_2$—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)$_2$O—, —N(R$^c$)N(R$^c$)C(S)O—, —N(R$^c$)N(R$^c$)C(N(R$^d$))O—, —OP(O)$_2$O—, —N(R$^c$)P(O)$_2$O—, —OP(O)$_2$N(R$^c$)—, —N(R$^c$)P(O)$_2$N(R$^c$)—, —P(O)$_2$O—, —P(O)$_2$N(R$^c$)—, —N(R$^c$)P(O)$_2$—, —OP(O)$_2$—, —O-alkyl-heterocycloalkyl-N(R)—, —NC)CHR$^d$C(O)N(R$^c$)CHR$^d$C(O)—, —N(R$^c$)CHR$^d$C(O)—N(R$^c$)C(O)CHR$^d$, or —C(O)N(R$^c$)CHR$^d$C(O)—; wherein R$^f$, R$^g$ and R$^h$, for each occurrence is H, alkyl, aryl, heteroaryl, aralkyl, cycloalkyl, or heterocycloalkyl;

R$_2$ and R$_4$, for each occurrence, are, independently, R$^c$, alkenyl, alkynyl, halogen, nitro, cyano, isothionitro, SR$^c$, or OR$^c$; or R$_2$ and R$_4$, taken together with the carbon to which they are attached, are a carbonyl;

R$_3$ is R$^c$, alkenyl, alkynyl, —OR$^c$, —OC(O)R$^c$, —SO$_2$R$^c$, —S(O)R$^c$, —S(O)$_2$NR$^c$R$^d$, —SR$^c$, —NR$^c$R$^d$, —NR$^c$COR$^d$, —NR$^c$C(O)R$^d$, —NR$^c$C(O)OR$^d$, —NR$^c$C(O)NR$^c$R$^d$, —NR$^c$SO$_2$R$^d$, —C(O)R$^c$, —C(O)OR$^c$, —C(O)NR$^c$R$^d$, —P(O)OR$^c$OR$^d$, or S(O)$_2$NR$^c$R$^d$;

R$_8$ and R$_9$ are each, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R$_8$ and R$_9$ taken together with the nitrogen to which they are attached are an optionally substituted heterocycloalkyl or an optionally substituted heteroaryl;

n is 0, 1, 2, 3, 4, 5, or 6;

m is 0 or 1;

Y is O, S, or NR$^c$;

R$^c$ and R$^d$, for each occurrence, are, independently, H, alkyl, aryl, aralkyl, heteroaryl, heteroaralkyl, cycloalkyl, heterocycloalkyl, —C(O)-alkyl, or —S(O)$_2$R$_f$; and R$^e$ is a lower alkyl.

Compounds represented by formula (VIa) or regioisomeric mixtures that include compounds represented by formula (VIa) are useful in preparing compounds represented by formula (I), or a pharmaceutically acceptable salt, solvate, clathrate, hydrate, polymorph or prodrug thereof.

In one embodiment, in compounds represented by formulas (VIa), (VIb), and/or (VIc), R$_3$ is an optionally substituted pyridinyl, such as pyridine-2-yl, pyridine-3-yl, and 1-oxo-pyridine-2-yl.

In another embodiment, in compounds represented by formulas (VIa), (VIb), and/or (VIc), R$_3$ is pyrid-2-on-1-yl.

In another embodiment, in compounds represented by formulas (VIa), (VIb), and/or (VIc), R$_3$ is an optionally substituted phenyl, such as phenyl and 3,4-dimethoxy-phenyl.

In another embodiment, in compounds represented by formulas (VIa), (VIb), and/or (VIc), R$_3$ is hydroxy.

In another embodiment, in compounds represented by formulas (VIa), (VIb), and/or (VIc), R$_3$ is [1,3]dioxin-2-yl.

In another embodiment, in compounds represented by formulas (VIa), (VIb), and/or (VIc), R$_3$ is an alkoxy, such as methoxy.

In another embodiment, in compounds represented by formulas (VIa), (VIb), and/or (VIc), R$_3$ is 2,2-dimethyl-[1,3]dioxolan-4-yl.

In another embodiment, in compounds represented by formulas (VIa), (VIb), and/or (VIc), R$_3$ is an alkyl.

In another embodiment, in compounds represented by formulas (VIa), (VIb), and/or (VIc), R$_3$ is a group represented by —C(O)OR$^c$, such as —C(O)OCH$_2$CH$_3$.

In another embodiment, in compounds represented by formulas (VIa), (VIb), and/or (VIc), n is 1 or 2 and m is 0.

In another embodiment, in compounds represented by formulas (VIa), (VIb), and/or (VIc), n is 1 or 2 and m is 1.

In another embodiment, in compounds represented by formulas (VIa), (VIb), and/or (VIc), Y is —O—.

In another embodiment, in compounds represented by formulas (VIa), (VIb), and/or (VIc), G is —O— and m is 1.

In another embodiment, in compounds represented by formulas (VIa), (VIb), and/or (VIc), X is —NH—.

In another embodiment, in compounds represented by formulas (VIa), (VIb), and/or (VIc), X is —O—.

In another embodiment, in compounds represented by formulas (VIa), (VIb), and/or (VIc), —NR$_8$R$_9$ is an optionally substituted heterocycloalkyl ring, such as morpholine.

In another embodiment, in compounds represented by formulas (VIa), (VIb), and/or (VIc), R$_8$ and R$_9$ are each independently an optionally substituted alkyl, such as methyl, ethyl, n-propyl, isopropyl, and the like.

In another embodiment, in compounds represented by formulas (VIa), (VIb), and/or (VIc), R$_8$ and R$_9$ are both methyl.

In another embodiment, in compounds represented by formulas (VIa), (VIb), and/or (VIc), R$_2$ and R$_4$ are both —H, and n is an integer from 1 to 6.

In another embodiment, in compounds represented by formulas (VIa), (VIb), and/or (VIc), R$_2$ and R$_4$ are both —H, and n is an integer from 1 to 2.

In another embodiment, in compounds represented by formulas (VIa), (VIb), and/or (VIc), R$_2$ and R$_4$ are —H, n is an integer from 1 to 2, and Y is —O—.

In another embodiment, the compound represented by formula (VIa) is 2-[2-(pyridine-2-yl)-ethoxy]-4-hydrazino-6-(morpholin-4-yl)-pyrimidine.

1.1.1 Exemplary Compounds of the Invention

Exemplary compounds which can be prepared by the processes of the invention are depicted in Table 1 below, including pharmaceutically acceptable salts thereof.

TABLE 1

| No. | Compound | Name |
|---|---|---|
| 1 | | 2-(butoxy)-4-[N'-(1H-indol-3-ylmethylene)-hydrazino]-6-(morpholin-4-yl)-pyrimidine |

TABLE 1-continued

| No. | Compound | Name |
|---|---|---|
| 2 | | 2-(3-hydroxy-propylsulfanyl)-4-[N'-(1H-indol-3-ylmethylene)-hydrazino]-6-(morpholin-4-yl)-pyrimidine |
| 3 | | 2-(2,2-Dimethyl-[1,3]dioxolan-4-ylmethoxy)-4-[N'-(1H-indol-3-ylmethylene)-hydrazino]-6-(morpholin-4-yl)-pyrimidine |
| 4 | | 2-[2-(3,4-Methoxy-phenyl)-ethoxy]-4-[N'-(1H-indol-3-ylmethylene)-hydrazino]-6-(morpholin-4-yl)-pyrimidine |
| 5 | | 2-[2-(Pyridin-2-yl)-ethoxy]-4-[N'-(1H-indol-3-ylmethylene)-hydrazino]-6-(morpholin-4-yl)-pyrimidine |
| 6 | | 2-[2-(Pyridin-2-yl)-ethoxy]-4-N'-(3-methyl-benzilidene)-hydrazino]-6-(morpholin-4-yl)-pyrimidine |

TABLE 1-continued

| No. | Compound | Name |
|---|---|---|
| 7 | | 2-[2-(Pyridin-2-yl)-ethoxy]-4-[N'-(3-ethyl-benzilidene)-hydrazino]-6-(morpholin-4-yl)-pyrimidine |
| 8 | | 2-[2-(Pyridin-2-yl)-ethoxy]-4-[N'-(1-meta-tolyl-ethylidene)-hydrazino]-6-(morpholin-4-yl)-pyrimidine |
| 9 | | 2-[2-(Pyridin-2-yl)-ethoxy]-4-[N'-(1H-indol-3-ylmethylene)-N-methyl-hydrazino]-6-(morpholin-4-yl)-pyrimidine |
| 10 | | 2-[2-(Pyridin-2-yl)-ethoxy]-4-(3-methyl-benzilideneaminooxy)-6-(morpholin-4-yl)-pyrimidine |
| 11 | | 2-[2-(Pyridin-2-yl)-ethoxy]-4-(1H-indol-3-ylmethyleneaminooxy)-6-(morpholin-4-yl)-pyrimidine |

| No. | Compound | Name |
| --- | --- | --- |
| 12 | | 2-[2-(Pyridin-2-yloxy)-ethoxy]-4-[N'-(1H-indol-3-ylmethylene)-hydrazino]-6-(morpholin-4-yl)-pyrimidine |
| 13 | | 2-[2-(Pyridin-2-yloxy)-ethoxy]-4-[N'-(3-methyl-benzilidene)-hydrazino]-6-(morpholin-4-yl)-pyrimidine |
| 14 | | 2-(Butylamino)-4-[N'-(1H-indol-3-ylmethylene)-hydrazino]-6-(morpholin-4-yl)-pyrimidine |
| 15 | | 2-(Pyridin-3-yloxy)-4-[N'-(3-methyl-benzilidene)-hydrazino]-6-(morpholin-4-yl)-pyrimidine |
| 16 | | 2-[2-(2-Oxo-2H-pyridin-1-yl)-ethoxy]-4-[N'-(3-methyl-benzilidene)-hydrazino]-6-(morpholin-4-yl)-pyrimidine |

| No. | Compound | Name |
|---|---|---|
| 17 | | 2-[2-(Pyridin-2-yl)-ethoxy]-4-[N'-(3-iodo-benzilidene)-hydrazino]-6-(morpholin-4-yl)-pyrimidine |
| 18 | | 2-[2-(Pyridin-2-yl)-ethoxy]-4-[N'-(3-fluoro-benzilidene)-hydrazino]-6-(morpholin-4-yl)-pyrimidine |
| 19 | | 2-[2-(Pyridin-2-yl)-ethoxy]-4-[N'-(3-chloro-benzilidene)-hydrazino]-6-(morpholin-4-yl)-pyrimidine |
| 20 | | 2-[2-(Pyridin-2-yl)-ethoxy]-4-[N'-(3-methoxycarbonyl-benzilidene)-hydrazino]-6-(morpholin-4-yl)-pyrimidine |
| 21 | | 2-[2-(Pyridin-2-yl)-ethoxy]-4-[N'-(3-methylcarbamoyl-benzilidene)-hydrazino]-6-(morpholin-4-yl)-pyrimidine |
| 22 | | 2-[2-(Pyridin-2-yl)-ethoxy]-4-[N'-(3-hydroxymethyl-benzilidene)-hydrazino]-6-(morpholin-4-yl)-pyrimidine |

TABLE 1-continued

| No. | Compound | Name |
|---|---|---|
| 23 | | 2-[2-(2-Oxo-2H-pyridin-1-yl)-ethoxy]-4-[N'-(3-iodo-benzilidene)-hydrazino]-6-(morpholin-4-yl)-pyrimidine |
| 24 | | 2-[2-(1-Oxo-pyridin-2-yl)-ethoxy]-4-[N'-(3-methyl-benzilidene)-hydrazino]-6-(morpholin-4-yl)-pyrimidine |

2. EXAMPLES

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

Synthesis of 2-[2-(pyridin-2-yl)-ethoxy]-4-[N'-(3-methyl-benzilidene)-hydrazino]-6-(morpholin-4-yl)-pyrimidine (Compound 6)

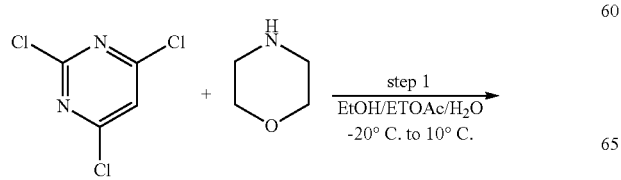

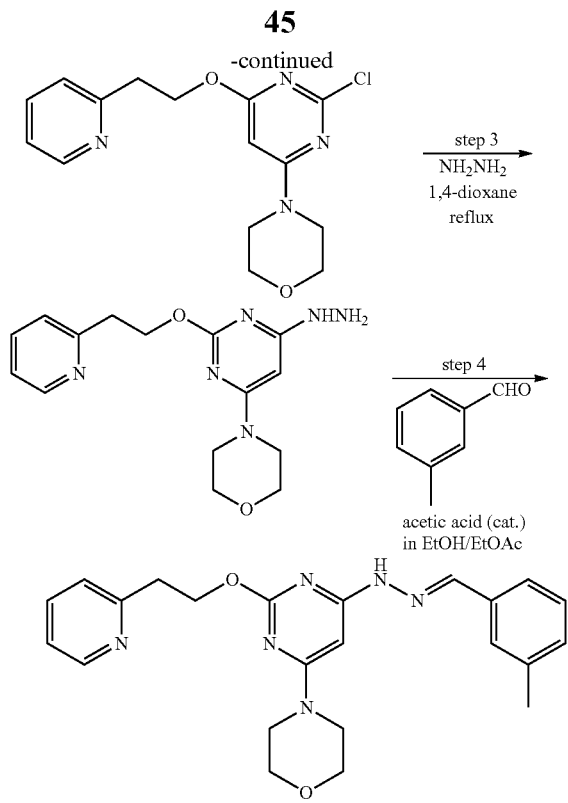

Step 1.

A 2-liter, 3-neck flask equipped with mechanical stirrer, thermometer and dropping funnel was loaded with ethanol (375 mL), water (375 mL) and morpholine, (1.01 mol, 88 g); the resulting solution was cooled (with sodium chloride-ice mixture) to about 0° C. and a solution of 2,4,6-trichloropyrimidine (91.17 g, 0.5 mol) in ethyl acetate (37.5 mL) was added dropwise in about 20 minutes, to maintain temperature below 10° C. The dropping funnel was rinsed twice with ethyl acetate (3 mL), and the rinses were transferred to the reaction mixture. The reaction was checked by TLC to determine when the reaction was complete. After completion of the reaction, ice water (375 mL) was added, and reaction was allowed to stir for 30 minutes to complete precipitation. The colorless solid was filtered out, washed 6 times with water (225 mL per wash) and vacuum-dried at 40-50° C. until a constant weight of the product was maintained. The product (114.7 g, 98% yield) was a mixture of regioisomers 2,4-dichloro-6-(morpholin-4-yl)-pyrimidine and 4,6-dichloro-2-(morpholin-4-yl)-pyrimidine in about a 3.9:1 ratio (Product 1).

Step 2.

Product 1 (114.7 g, 0.49 mol) and 2-(2-hydroxyethyl)-pyridine, 98% (64.66 g, 0.514 mol) were dissolved in anhydrous DMF (539 mL) and cooled to 0° C. Sodium hydride, 60% dispersion in oil, (23.52 g, 0.588 mol) was added under nitrogen purge to the vigorously stirred reaction mixture in 6 portions, to maintain the reaction temperature below 5° C. The reaction was stirred for 30 minutes, then checked by TLC to determine completion of the reaction. When the reaction was complete, heptane (107.7 mL, 0.735 mol) was added, and the reaction was allowed to stir for additional 1.5 hours at room temperature before it was carefully quenched with ice water (539 mL) and left overnight for precipitation to be completed. The precipitated solid was filtered out, washed 3 times with water (245 mL per wash), then 3 times with heptane (98 mL per wash), and vacuum-dried at 40-50° C. until constant weight was maintained to yield Product 2 (97.4 g, 62% yield) as a mixture of regioisomers. Product 2 contained the desired regioisomer, 2-[2-(pyridin-2-yl)-ethoxy]-4-chloro-6-(morpholin-4-yl)-pyrimidine (88%), as well as 4-[2-(pyridin-2-yl)-ethoxy]-6-chloro-2-(morpholin-4-yl)-pyrimidine and 6-[2-(pyridin-2-yl)-ethoxy]-2-chloro-4-(morpholin-4-yl)-pyrimidine which together made up less than 12%.

Step 3.

A stirred suspension of Product 2 (97.4 g, 0.304 mol) and hydrazine monohydrate (53.2 g, 1.06 mol) in dioxane (188 mL) was brought to boil under nitrogen purge, and was refluxed for 5 hours. Ice water (376 mL) was added to the reaction mixture, and the mixture was allowed to stand overnight. A resulted precipitate was filtered out, washed 3 times with water (260 mL per wash) and vacuum-dried at 40-50° C. until constant weight was maintained to yield Product 3 (70.2 g, 73% yield) as one regioisomer, 2-[2-(pyridin-2-yl)-ethoxy] 4-hydrazino-6-(morpholin-4-yl)-pyrimidine.

Step 4.

A stirred suspension of Product 3 (70.2 g, 0.22 mol), m-tolyl aldehyde (28 g, 0.23 mol) and catalytic amount of acetic acid (0.67 g, 11 mmol) in absolute ethanol-ethyl acetate mixture (1:1 by volume, 162 mL of each) was heated until a clear solution (55-75° C.) was formed and TLC indicated that all starting material was consumed (at least 30 minutes). The reaction mixture was cooled down to 30° C. and filtered. The reactor and filter were washed with ethanol-ethyl acetate 1:1 mixture (80 mL of each), and the combined filtrate and washings were concentrated to an oily mixture having about one-third of initial solvent volume. To facilitate precipitation, the oily mixture was stirred for at least 2 hours (or up to 12 hours). The solid was filtered out, washed twice with absolute ethanol (115 mL per wash) and dried. 2-[2-(Pyridin-2-yl)-ethoxy]-4-[N'-(3-methyl-benzilidene)-hydrazino]-6-(morpholin-4-yl)-pyrimidine (Compound 6) was obtained as an off-white or colorless solid (90.2 g, 97% yield) having a purity of greater than 98%.

To achieve a higher purity, a suspension of 2-[2-(pyridin-2-yl)-ethoxy]4-[N'-(3-methyl-benzilidene)-hydrazino]-6-(morpholin-4-yl)-pyrimidine (88.3 g, 0.21 mol) in absolute ethanol (400 mL) was heated to reflux and refluxed until a clear solution was formed. About 200 mL of ethanol was removed from the solution under reduced pressure, and the mixture was stirred at room temperature until precipitation was completed (about 3 hours). The precipitate was filtered out, washed twice with ethanol (100 mL) and vacuum-dried at 40-50° C. until constant weight was maintained to yield 2-[2-(pyridin-2-yl)-ethoxy]-4-[N'-(3-methyl-benzilidene)-hydrazino]-6-(morpholin-4-yl)-pyrimidine as a colorless solid (81.2 g, 90% yield for the recrystallization step) of greater than 99.5% purity.

Example 2

Alternative synthesis of 2-[2-(pyridin-2-yl)-ethoxy]-4-[N'-(3-methyl-benzilidene)-hydrazino]-6-(morpholin-4-yl)-pyrimidine (Compound 6)

A stirred suspension of 2-[2-(pyridin-2-yl)-ethoxy]-4-hydrazino-6-(morpholin-4-yl)-pyrimidine (Product 3) (5 g, 15.8 mmol, 95% purity), m-toluadehyde (1.99 g, 16.6 mmol), ethyl acetate (25 mL) and acetic acid (45 µL) was heated to reflux for 15 minutes to give a clear solution. When TLC indicated that the reaction was completion, the reaction was allowed to cool to room temperature causing a solid precipitate to formed. The creamy solid was filtered out, washed with ethyl acetate (EtOAc) (3×5 mL) and dried to obtain crude Compound 6. The crude product (5 g, 75.6%) was dissolved in EtOAc (34 mL) under reflux. The resulting clear solution was concentrated to about 20 mL and cooled to room temperature causing Compound 6 to precipitate out forming a suspension. The suspension was stirred for 2 hours, then the precipitate was filtered out, washed with EtOAc (2×10 mL) and vacuum-dried to give Compound 6 as an off-white solid, 4.1 g (82%).

All publications, patent applications, patents, and other documents cited herein are incorporated by reference in their entirety. In case of conflict, the present specification, including definitions, will control. In addition, the materials, methods, and examples are illustrative only and not intended to be limiting.

We claim:

1. A method for regioselectively preparing a compound represented by formula (I):

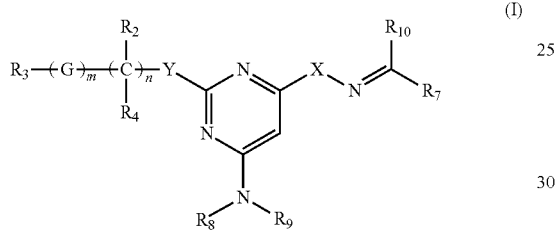

or a salt thereof, wherein:

X is —NH—;

G is —O—, —O—C(O)—NH—, —O—C(O)—NR$^f$—, —O—C(S)—NH—, —NH—C(S)—O—, —O—C(S)—NR$^f$—, —NR$^c$C(S)—O—, —P(O)(R$^c$)—, —P(O)(R$^c$)—O—, —P(O)(R$^c$)—NR$^c$—, -Cyclyl-, -Heterocycloalkyl-, -Aryl-, -Heteroaryl-, -Heteroaralkyl-, -Heteroaryl-NH—, -Heteroaryl-S—, -Heteroaralkyl-O—, —Si(OH)$_2$—, —B(OH)—, —P(O)$_2$O—, —P(O)$_2$N(R$^c$)—, —N(R$^c$)P(O)$_2$, or —OP(O)$_2$—; wherein R$^f$ for each occurrence is H, alkyl, aryl, heteroaryl, aralkyl, cycloalkyl, or heterocycloalkyl;

R$_2$ and R$_4$ are each H;

R$_3$ is R$^c$, alkenyl, alkynyl, —OR$^c$, —OC(O)R$^c$, —SO$_2$R$^c$, —S(O)R$^c$, —S(O)$_2$NR$^c$R$^d$, —SR$^c$, —NR$^c$R$^d$, —NR$^c$COR$^d$, —NR$^c$C(O)R$^d$, —NR$^c$C(O)OR$^d$, —NR$^c$C(O)NR$^c$R$^d$, —NR$^c$SO$_2$R$^d$, —C(O)R$^c$, —C(O)OR$^c$, —C(O)NR$^c$R$^d$, —P(O)OR$^c$OR$^d$, or —S(O)$_2$NR$^c$R$^d$;

R$_7$ is an optionally substituted indolyl or an optionally substituted phenyl;

R$_8$ and R$_9$, taken together with the nitrogen to which they are attached, are an optionally substituted heterocycloalkyl, wherein the heterocycloalkyl is morpholine;

R$_{10}$ is H or methyl;

n is 1 or 2;

m is 0 or 1;

Y is O, S, or NR$^c$; and

R$^c$ and R$^d$, for each occurrence, are, independently, H, alkyl, aryl, aralkyl, heteroaryl, heteroaralkyl, cycloalkyl, heterocycloalkyl, —C(O)-alkyl, or —S(O)$_2$R$_f$;

the method comprising the steps of:

a) reacting HNR$_8$R$_9$ with a 2,4,6-trihalopyrimidine in a solution of alcohol and water, wherein HNR$_8$R$_9$ is present in an excess amount compared to the 2,4,6-trihalopyrimidine, to form a first mixture of regioisomers represented by formulas (IIIa) and (IIIb):

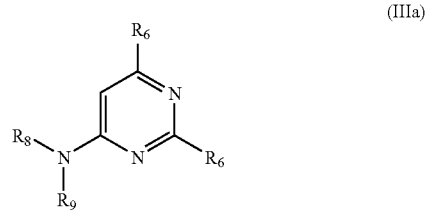

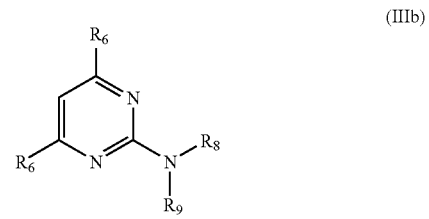

wherein R$_6$, for each occurrence, is independently F, Cl, Br, or I;

b) adding a strong base to the first mixture in at least 2 separate portions, and the mixture is maintained at a temperature of between about −20° C. and about 10° C., comprising the regioisomers represented by formulas (IIIa) and (IIIb) and a compound represented by formula (II):

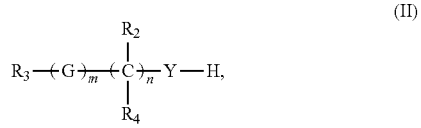

thereby forming a second mixture of regioisomers represented by formulas (IVa), (IVb), and (IVc):

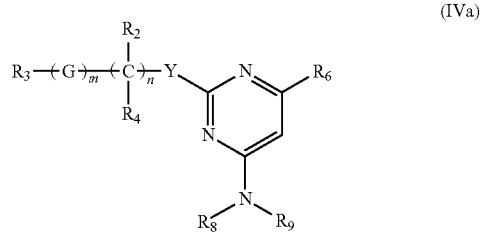

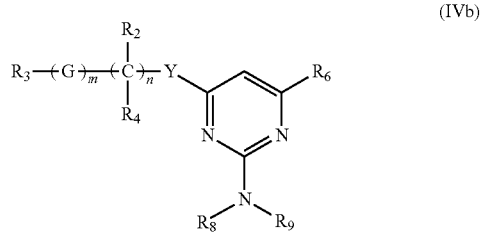

-continued

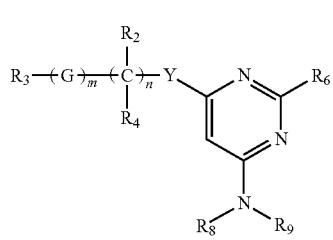
(IVc)

c) adding a hydrocarbon solvent to the second mixture after the reaction is substantially complete and stirring the mixture for between about 1 hour to about 2 hours;

d) heating a suspension comprising hydrazine, and the regioisomers represented by formulas (IVa), (IVb), and (IVc) in a polar solvent, thereby forming a third mixture comprising regioisomers represented by formulas (VIa), (VIb) and (VIc):

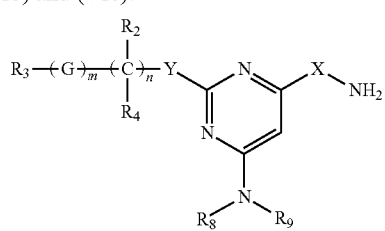
(VIa)

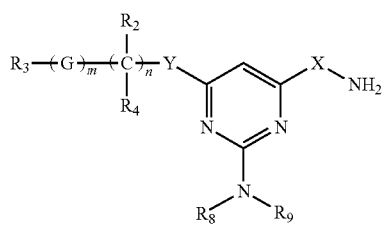
(VIb)

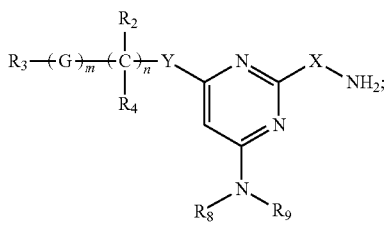
(VIc)

e) adding water to the third mixture of regioisomers represented by formulas (VIa), (VIb), and (VIc), wherein the volume of water added is about 1 to about 4 times the volume of the polar solvent;

f) allowing the compound represented by formula (VIa) to selectively precipitate out of the mixture at room temperature;

g) collecting the precipitate comprising a compound represented by formula (VIa);

h) heating in the presence of a catalytic amount of an acid the precipitate comprising a compound represented by formula (VIa) and a compound represented by the formula $R_7$—$C(O)R_{10}$, thereby regioselectively forming a compound represented by formula (I).

2. The method of claim 1, further comprising the step of recrystallizing the compound represented by formula (I) in ethanol.

3. The method of claim 1, wherein the polar solvent in step d) is selected from the group consisting of an ether, dimethylacetamide (DMA), N-methylpyrrolidine (NMP), tetrahydrofuran (THF), a dioxane, hexamethylphosphoramide (HMPA), or mixtures thereof.

4. The method of claim 1, wherein the polar solvent is 1,4-dioxane and the reaction mixture in step d) is heated to between about 80° C. and about 105° C.

5. The method of claim 1, wherein the compound represented by formula (VIa) is allowed to precipitate for between about 2 to about 12 hours in step f).

6. The method of claim 1, wherein the compound represented by formula (VIa) and $R_7$—$C(O)R_{10}$ are heated in ethyl acetate in the presence of a catalytic amount of an acid.

7. The method of claim 1, wherein the compound represented by formula (I) is at least about 70% pure.

8. The method of claim 1, wherein the compound represented by formula (I) is at least about 80% pure.

* * * * *